US008074649B2

(12) United States Patent
Dhuper et al.

(10) Patent No.: US 8,074,649 B2
(45) Date of Patent: Dec. 13, 2011

(54) ENDOTRACHEAL TUBE WITH FEATURE FOR DELIVERING AEROSOLIZED MEDICATION

(75) Inventors: Sunil Kumar Dhuper, Old Westbury, NY (US); Sarita Dhuper, Old Westbury, NY (US)

(73) Assignee: Aeon Research and Technology, Inc., Hewlett, NY (US)

( * ) Notice: Subject to any disclaimer, the term of this patent is extended or adjusted under 35 U.S.C. 154(b) by 835 days.

(21) Appl. No.: 10/197,396

(22) Filed: Jul. 18, 2002

(65) Prior Publication Data

US 2004/0011364 A1 Jan. 22, 2004

(51) Int. Cl.
*A61M 16/00* (2006.01)
*A62B 9/06* (2006.01)

(52) U.S. Cl. ......... 128/207.14; 128/202.27; 128/203.12; 128/203.15

(58) Field of Classification Search ............. 128/200.14, 128/200.16, 200.21, 200.22, 200.23, 202.27, 128/203.12, 203.15, 207.14
See application file for complete search history.

(56) References Cited

U.S. PATENT DOCUMENTS

| | | | |
|---|---|---|---|
| 2,796,295 | A | 6/1957 | McKinnon |
| D184,636 | S | 3/1959 | Pickerell et al. |
| 2,906,265 | A | 9/1959 | Samuels |
| 2,990,563 | A | 7/1961 | Davidson |
| 3,104,062 | A | 9/1963 | Mahon |
| D198,964 | S | 8/1964 | Dash et al. |
| 3,184,115 | A | 5/1965 | Meshberg |
| D206,979 | S | 2/1967 | Jaffe |
| D207,143 | S | 3/1967 | Goodwin |
| 3,826,413 | A | 7/1974 | Warren |
| D233,845 | S | 12/1974 | Fettel et al. |
| 4,114,811 | A | 9/1978 | Loeffler |
| D251,203 | S | 2/1979 | Williamson |
| 4,190,046 | A | 2/1980 | Virag |
| D258,535 | S | 3/1981 | Reichl |
| 4,291,688 | A | 9/1981 | Kistler |
| D262,320 | S | 12/1981 | Mono |
| D264,940 | S | 6/1982 | Stock |
| D272,094 | S | 1/1984 | Wolf et al. |
| 4,584,998 | A | 4/1986 | McGrail |
| 4,669,463 | A | 6/1987 | McConnell |
| 4,711,378 | A | 12/1987 | Anderson |
| D294,175 | S | 2/1988 | Briggs |
| 4,821,714 | A | 4/1989 | Smelser |
| 4,830,224 | A | 5/1989 | Brison |
| D304,232 | S | 10/1989 | Fuller |
| D307,183 | S | 4/1990 | Kalayjian |
| 5,078,131 | A * | 1/1992 | Foley ...................... 128/203.15 |

(Continued)

*Primary Examiner* — Gary Jackson
*Assistant Examiner* — Michael Mendoza
(74) *Attorney, Agent, or Firm* — Leason Ellis LLP

(57) ABSTRACT

Current methods of drug administration to the lungs are inefficient. 'Endotracheal Tube with Aerosol Delivery Apparatus III' is specifically designed for uniform intrapulmonary delivery of aerosolized medication in patients on mechanical ventilation. As opposed to the current methods of drug delivery where aerosol particles are generated at the proximal end of the ETT, with majority of the particles adhering to the endotracheal tube during delivery, this invention bypasses the endotracheal tube by generating aerosol particles at its distal end. The invention consists of two coaxial hollow tubes fused to each other. The inner coaxial tube and/or one or more secondary cannulation(s) in the wall of the outer coaxial tube terminate at proximal and as MDI adapters and at the distal tip as a single or multiple micrometric orifices. The device generates one or more aerosol plumes with different geometries, velocities and orientations made possible by variations in the ID, shape, trajectory and orientation of secondary cannulation(s) and the distal orifice(s) to ensure effective aerosol delivery to respiratory system.

14 Claims, 17 Drawing Sheets

U.S. PATENT DOCUMENTS

| | | |
|---|---|---|
| D328,244 S | 7/1992 | Hamilton et al. |
| 5,146,936 A | 9/1992 | Ng |
| D335,175 S | 4/1993 | Sladek |
| 5,357,946 A * | 10/1994 | Kee et al. .................. 128/200.24 |
| 5,504,224 A | 4/1996 | Wilson |
| 5,542,412 A | 8/1996 | Century |
| 5,570,686 A | 11/1996 | Century |
| 5,579,758 A | 12/1996 | Century |
| 5,594,987 A | 1/1997 | Century |
| 5,606,789 A | 3/1997 | Century |
| 5,642,730 A | 7/1997 | Baran |
| 5,964,223 A * | 10/1999 | Baran ..................... 128/207.14 |
| 6,079,413 A | 6/2000 | Baran |

\* cited by examiner

ENDOTRACHEAL TUBE WITH FEATURE FOR DELIVERING AEROSOLIZED MEDICATION

CROSS-REFERENCE TO RELATED APPLICATIONS

| | | | |
|---|---|---|---|
| 2,796,295 | June 1957 | McKinnon | 239/356 |
| D184,636 | March 1959 | Pickerell et al. | D9/301 |
| 2,906,265 | September 1959 | Samuels | D24/110 |
| 2,990,563 | July 1961 | Davidson | D24/119 |
| 3,104,062 | September 1963 | Mahon | D24/62 |
| D198,964 | August 1964 | Dash et al. | D24/115 |
| 3,184,115 | May 1965 | Meshberg | 128/200 |
| D206,979 | February 1967 | Jaffe | D24/62 |
| D207,143 | March 1967 | Goodwin | D24/62 |
| 3,826,413 | July 1974 | Warren | 128/200 |
| D233,845 | December 1974 | Fettel et al. | D24/129 |
| 4,114,811 | September 1978 | Loeffler | 128/400 |
| D251,203 | February 1979 | Williamson | D9/352 |
| 4,190,046 | February 1980 | Virag | 128/200 |
| D258,535 | March 1981 | Reichl | D24/62 |
| 4,291,688 | September 1981 | Kistler | 128/400 |
| D262,320 | December 1981 | Mono | D24/62 |
| D264,940 | June 1982 | Stock | D9/355 |
| D272,094 | January 1984 | Wolf et al. | D24/110 |
| 4,711,378 | December 1987 | Anderson | 222/206 X |
| D294,175 | February 1988 | Briggs | D24/62 |
| 4,830,224 | May 1989 | Brison | 222/402 |
| D304,232 | October 1989 | Fuller | D24/110 |
| D307,183 | April 1990 | Kalayjian | D24/110 |
| D328,244 | July 1992 | Hamilton et al. | D24/110 X |
| D335,175 | April 1993 | Sladek | D24/110 |
| 5,542,412 | August 1996 | Century | 128/203 |
| 5,570,686 | November 1996 | Century | 128/203 |
| 579,758 | January 1997 | Century | 441/60 |
| 5,594,987 | January 1997 | Century | 29/890 |
| 5,606,789 | March 1997 | Century | 29/281 |
| 5,964,223 | October 1999 | Baran | 128/207 |
| 6,079,413 | June 2000 | Baran | 128/207 |

STATEMENT REGARDING FEDERALLY SPONSORED RESEARCH OR DEVELOPMENT

Not Applicable

REFERENCE TO A SEQUENCE LISTING, A TABLE, OR A COMPUTER PROGRAM LISTING COMPACT DISK APPENDIX

Not Applicable

REFERENCE TO THE RELATED APPLICATION

The present application incorporates by reference the co pending application entitled "AEROSOL DELIVERY APPARATUS-VCA & MDA" found by the same inventor of the present application and on the even date here with and assigned Ser. No. 10/099,210.

BACKGROUND OF THE INVENTION

The present invention, "AEROSOL DELIVERY APPARATUS III", relates to medical-surgical devices designed for improved intrapulmonary deposition of aerosol particles both quantitatively as well as qualitatively in patients on mechanical ventilation via endotracheal tube. Multiple medications readily lend themselves for pulmonary administration. Many diagnostic and therapeutic agents that can be utilized through this route are the bronchodilators, anti-inflammatory agents like steroids, antibiotics, anticholinergics, heparin, surfactant, antiproteases, gene transfer products, insulin, radioactive dyes, etc.

The advantages of intrapulmonary drug delivery as opposed systemic administration are well known. The desired effect at the site of local delivery as opposed to systemic administration minimizes side effects and is the preferred methodology for delivery of several medications. Conventional methods for aerosol delivery have resulted in failure of effective drug delivery to the lungs. They are limited not only in total dose delivery but have also failed to achieve uniform intrapulmonary drug distribution. The two methods currently available for intrapulmonary drug delivery are highly inefficient. They are:

(I). Liquid bolus: The medication is instilled in the form of liquid bolus via a bronchoscope or through an ETT. The distribution by this method is non-uniform. Also there is a significant risk of inducing respiratory distress and hypoxemia.

(II) Aerosol Inhalation: Conventional methods of aerosol drug delivery have employed Metered Dose Inhalers (MDI's) with low boiling point propellants (CFC, HFA) or aerosol particles generated by heat, traditional compressed air nebulizers, or ultrasonic nebulizers. Even though these methods produce aerosol particles in respirable range (<5 microns) compared with the liquid bolus medication, they are limited in total dose delivery and lack-uniform distribution of medication to the lungs. Only a small fraction of the medication reaches the lungs as the majority of the aerosol particles either adhere to the nasal passages and oropharynx or are exhaled out. Efficiency of aerosol delivery drops even further in patients who are intubated and require mechanical ventilation.

Beck et al found that inhalation of nebulized material through an endotracheal tube resulted in deposition of only 1.87% of the delivered particles to the lungs. Methods employing a combined ventilator dispenser and adapter (U.S. Pat. No. 335,175) or other spacer devices with MDI's have revealed equally poor results as most of the aerosol particles adhere to the ETT, the connectors and the inspiratory limb of the corrugated plastic tube.

Investigators over the years have designed numerous endotracheal tubes in an attempt to overcome the hurdles associated with conventional methods of drug delivery to the respiratory system in patients on mechanical ventilation. Most designs of endotracheal tubes so far have only addressed the issue of drug delivery in the form of liquid bolus by incorporating drug irrigation devices in the traditional ETT in the form of secondary canalization with multiple micrometric openings (U.S. Pat. No. 5,146,936).

Factors that influence uniform delivery of aerosol particles in the tracheobronchial tree are the mid-mean diameter of aerosol particles (which should be in the respirable range, i.e. <5 microns), velocity of the aerosol plume, geometry of the aerosol plume (narrow vs. wide), site of the plume generation (proximal to ETT, distal to ETT, or in the lumen of the ETT), orientation of the plume (central vs. eccentric), time of actuation of MDI in the respiratory cycle, temperature and humidity in the respiratory circuit, etc. These features have not been addressed by any of the currently available endotracheal tubes incorporating drug irrigation devices.

U.S. Pat. No. 4,584,998 to McGrail describes an ETT with up to three secondary lumens in addition to the primary lumen in which one lumen can serve the purpose of delivering atomized gases to the patient.

U.S. Pat. No. 4,669,463 to McConnell shows ETT with a secondary lumen in the wall of the main lumen to deliver liquid medication to the respiratory system.

U.S. Pat. No. 4,821,714 to Smelser also describes an ETT with a secondary lumen to deliver medication to the respiratory system. The second lumen splits into two branches that terminate as two orifices, one at the distal tip and other along the exterior wall of the ETT.

U.S. Pat. No. 5,504,224 to Anne M. Buret, Pam Jeblenski, and Robert A. Virag describes an ETT with a secondary lumen in the wall of the ETT that terminates at a perforation (Murphy eye). The single stream of medication splits when it impacts on the distal edge of the opening resulting in delivery of medication both internally and externally of the ETT.

U.S. Pat. No. 5,642,730 to George Baran later continued as U.S. Pat. No. 6,079,413 assigned to the same inventor describes a catheter system for delivery of aerosolized medicine for use with pressurized propellant canister. The system includes an extension catheter that has a length such that the proximal end is connected to the canister and the distal end is positioned in the primary lumen or secondary lumen of the ETT beyond its distal end in the respiratory system. The system is not practical for many reasons. The invention describes an extremely complex system for centering the device in the lumen of the ETT which would require a significant amount of time to be spent in the tracheobronchial tree prior to delivery of medication. Hence, there would be interference with the ventilatory function and increased airway resistance at the time of manipulation of the device in the tracheobronchial tree. Secondly the system is complex enough to require a highly trained member of the professional staff, especially MD to carry out the operation. This may not be possible as currently all methods of drug delivery to tracheobronchial tree in patients on mechanical ventilation require either nursing staff or respiratory therapists and not necessarily MD's. Thirdly the system for prevention of impaction losses, especially carinal impaction is extremely expensive and there is no data demonstrates that the system will function effectively. Overall the system described in the invention is not of any practical clinical utility and hence it is currently being used as an experimental tool in research laboratories.

U.S. Pat. No. 5,964,223 assigned to George Baran describes a nebulizing catheter system similar to U.S. Pat. No. 5,642,730. This system describes the flow of liquid medication through the lumen of a catheter which is nebulized at its tip by a flow of pressurized gas through a coaxial lumen.

U.S. Pat. Nos. 5,579,758, 5,594,987, 5,606,789, 5,513,630, 5,542,412, 5,570,686 show a delivery device for intratracheal administration of drug in aerosol form called 'Penn Century Intratracheal Aerosolizer (Microsprayer)' The clinical utility of this device in humans at this time is extremely limited because of its high cost and need for sterilization after every use and as such it is solely being used as a research tool.

In summary, none of the prior art medical devices provide means for effective local delivery of medication to the tracheobronchial tree of both lungs in a cost effective manner.

BRIEF SUMMARY OF THE INVENTION

The present invention relates to novel medical surgical devices with an improved system of delivering aerosolized medication to patient's respiratory system.

OBJECTS OF INVENTION

The main object of the present invention is to provide a modified 'AEROSOL DELIVERY SYSTEM' that serves the following purposes:

Aerosol drug delivery to tracheobronchial tree.

Generation and delivery of aerosol particles at the distal end of the ETT with mid mean diameter that will allow uniform distribution throughout the tracheobronchial tree.

Generation and delivery of aerosol particles at the distal end of the ETT such that a significant fraction of the aerosol particles reach the tracheobronchial tree without adherence to the ETT.

Inexpensive method of intrapulmonary drug delivery

Provide a system that does not interfere with the ventilatory function at the time of operation of the device in the tracheobronchial tree A simple and user friendly system such that the medication can be delivered by any healthcare provider other than MD nurses, nurse practitioners, respiratory therapists, physician assistants, etc.

To achieve all the objects without interfering with the primary functions of the ETT.

To achieve the objectives through a device that is in no way traumatic to the patient.

The defined objectives are obtained through our present invention 'AEROSOL DELIVERY APPARATUS III' that incorporates several new features. The new system uses a pressurized canister or a metered dose inhaler (MDI) to deliver aerosolized medication to respiratory system. MDI is a system that uses a pressurized canister that contains either a suspension of pulverized particles of medication in a liquid propellant or a solution of the medication along with a liquid propellant. When the canister is actuated, the mixture of medication and propellant is generated from the distal orifice of the nozzle of the canister. Since the essence of this invention disclosed herein does not relate specifically to the structure of an MDI device, the details of this construction will not be discussed herein. Means of making and using MDI are well known to those skilled in the art. 'AEROSOL DELIVERY APPARATUS III' has two parts-ventilator connector with adapter (VCA) and medication dispenser with adapter (MDA). Ventilator connector with adapter (VCA) is an L or T shaped connector, the vertical limb of which is attached to an ETT tube with the help of an adapter, and the horizontal limb is connected to the corrugated tubes of the ventilator through a wye (Y) connector. The horizontal limb of the connector has a port or an adapter through which medication dispenser with adapter (MDA) is introduced into the ETT and the tracheobronchial tree. This port or adapter remains plugged with a cap or a plug at the time when MDA is not in use. The lumen of this port is in straight line with the vertical limb of the VCA and hence the ETT, in order to facilitate the introduction and manipulation of MDA in the ETT and tracheobronchial tree. The VCA can remain as the permanent part of the circuit even when MDA device is not in use.

Medication dispenser adapter (MDA) is a hollow cylindrical tubular structure made of plastic material (polymer or silicone). The device consists of two coaxial cylindrical tubes, the inner coaxial tube positioned exactly in the center of the outer coaxial tube. The two tubes may be fused to each other at one position (preferably anterior) or more than one position (anterior, posterior, right lateral and/or left lateral). The wall that connects the two tubes may extend throughout the entire length of the two tubes of there may be points of fusion at variable intervals. The proximal end of the device fuses or is matable with MDI (metered dose inhaler) adapter. The MDI adapter has two parts: the peripheral solid cylindrical structure that fuses with the outer coaxial tube and an inner hollow cylindrical structure, the distal end of which fuses or matable with the inner coaxial tube. The proximal end of the central hollow cylindrical part of the MDI adapter forms the inlet port for the nozzle of MDI canister, which perfectly fits into it. Such arrangement enables the delivery of medication from the MDI adapter to the distal tip of the central coaxial tube on actuation of the MDI canister. Hence no additional design or system is required for centering the device in ETT or tracheobronchial tree. The outer circumference of the MDI adapter is designed such that it may perfectly fit into the adapter/port located on the horizontal limb of the VCA (ventilator connector with adapter). There are two elastic (stretchable) strings located in the wall of the outer coaxial tube at 3 o'clock and 9 o'clock positions. Each elastic string runs through the entire length of the outer coaxial tube with the distal end terminating at the tip of the outer coaxial tube and the proximal end terminating as a rotator knob on the proximal surface of the peripheral cylindrical part of the MDI adapter. Rotation of the right rotator knob directs the MDA device towards the right mainstem bronchus and rotation of the left rotator knob similarly directs the MDA device towards the left mainstem bronchus. Hence, this special feature of MDA device allows the device to be manipulated and advanced into right or left mainstem bronchi of the tracheobronchial tree and delivers the medication independently to each lung one at a time. Located in the proximal ⅓ and distal ⅓ segment of the outer coaxial tube are numerous secondary orifices that are in communication with the main lumen of the ETT, the tracheobronchial tree and the VCA. Hence, the presence of MDA in the ETT, main trachea, right mainstem or left mainstem bronchus does not interfere with the ventilatory function in any way. The length, the ID, OD and the thickness of the walls of the inner and outer coaxial tubes may be variable depending on the adult or pediatric ETT through which it is introduced. As the Aerosol Delivery Apparatus III can be introduced into the endotracheal tube all the way beyond the tip of the ETT and also into the right or left mainstem bronchus the aerosol particles could be delivered directly into the tracheobronchial tree, completely bypassing the ETT.

BRIEF DESCRIPTION OF THE SEVERAL VIEWS OF THE DRAWING

Further features of the present invention will become apparent in the accompanying drawings as well as the detailed description of the preferred embodiments.

FIGS. 7b and 7c are the expanded cross sectional views of Aerosol Delivery Apparatus III according to the alternative embodiments of the present invention as described in FIG. 7a.

FIGS. 10b and 10c are the expanded cross sectional views of Aerosol Delivery Apparatus III according to the alternative embodiments of the present invention as described in FIG. 10a.

FIG. 17b is a first cross-sectional view of the VCA of FIG. 17a.

FIG. 17c is a second cross-sectional view of the VCA of FIG. 17a.

FIG. 18a is a side perspective view of a medicament dispenser and adapter (MDA).

FIG. 18b is a side elevation view of the MDA of FIG. 18a.

FIG. 18c is a cross-sectional view of the MDA of FIG. 18a.

DETAILED DESCRIPTION OF THE INVENTION

Figure 1:
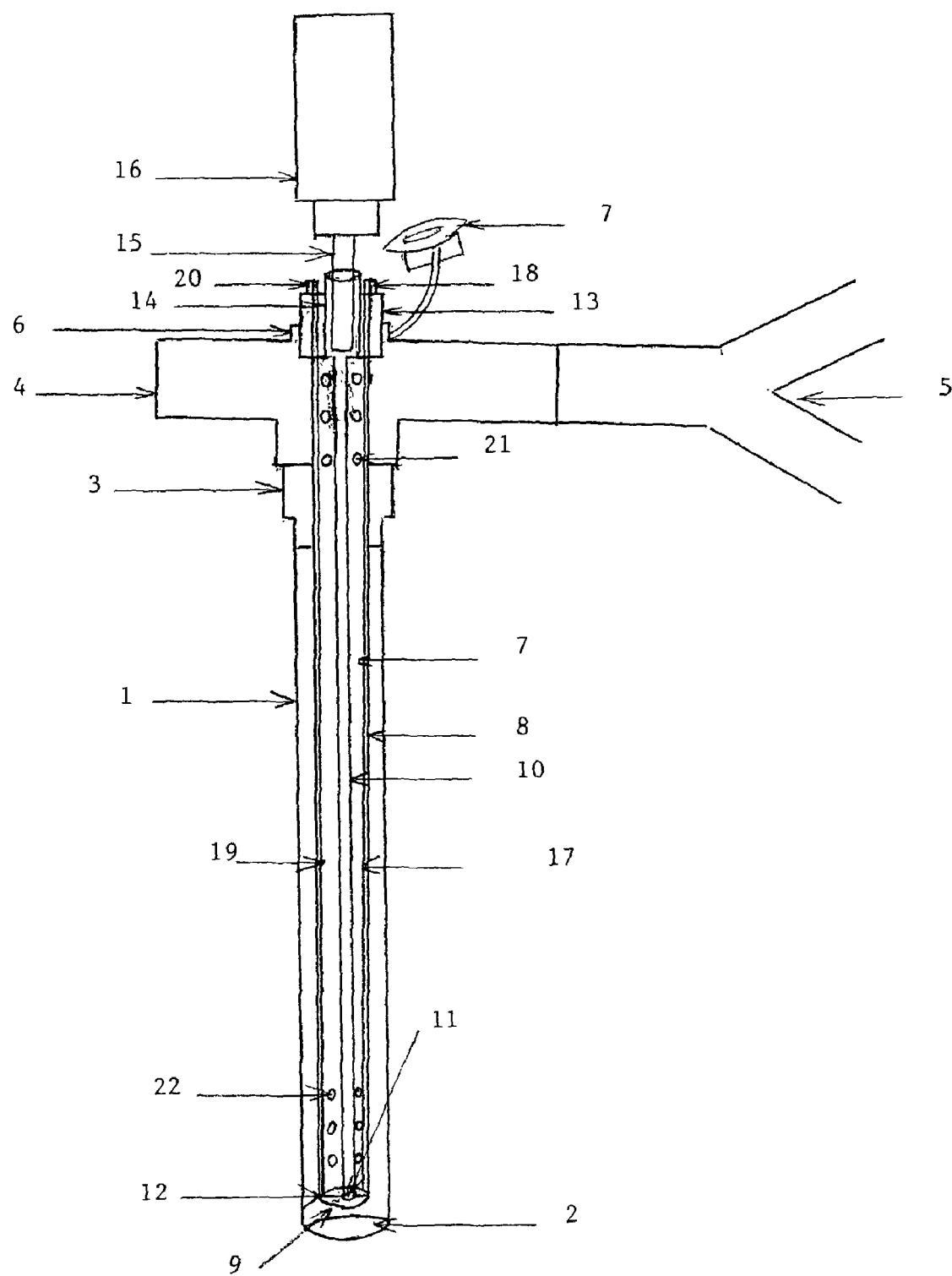
FIG. 1 is a plan view of the longitudinal length of Aerosol Delivery Apparatus III according to one embodiment of the present invention, incorporating the features described in the summary of the invention.

The present invention will now be described in detail by reference to the drawing figures, where as like parts as indicated by like reference numerals.

FIG. 1 is the first embodiment of the present invention that shows the longitudinal length of 'AEROSOL DELIVERY APPARATUS III'. The device is demonstrated in the lumen of an endotracheal tube (1), which may be a conventional adult or pediatric endotracheal tube (ETT). The ETT is an elongated hollow tube constructed from a plastic material (polymer) and is approximately 34 cm long if an adult size and smaller if pediatric. The internal diameter of the ETT may vary from 2.5 mm to 10 mm, the external diameter from 3.5 mm to 13 mm and the thickness of the wall from 0.5 mm to 2 mm. The tube is a flexible elongated conduit with a concave surface on one side and a convex surface on the opposite side. The ETT (1) has a distal lumen (2) and a proximal adapter (3) which enables it to be connected to a T or an L shaped ventilator connector with adapter (4). The ventilator connector with adapter (VCA) is connected to the elongated corrugated tubes of the ventilator via a wye (Y) connector (5).

The 'AEROSOL DELIVERY APPARATUS III' has two parts: ventilator connector with adapter (VCA) and medication dispenser with adapter (MDA). The VCA is a T or L shaped connector (4) demonstrated in FIG. 1. The vertical limb of the T or L is connected to the ETT via an adapter (3) and the horizontal limb is connected to the tubing of the ventilator via a wye connector (5). The horizontal limb of the VCA has an adapter or a port (6), which is in straight line with the vertical limb of VCA. The MDA is introduced into the ETT via the port (6) located on the horizontal limb of VCA. The port (6) may serve as an adapter that may perfectly fit the proximal end of the MDA. When not in use the port/adapter remains closed with the help of plug or a cap (7).

The second part of Aerosol Delivery Apparatus III is the medication dispenser with adapter (MDA). MDA is an elongated hollow tubular structure constructed from a plastic material (polymer or silicone). The length of MDA may be variable depending on adult or pediatric use. The MDA consists of two hollow cylindrical coaxial tubes, which may be fused with each other at one or more points along their circular edges. The points of fusion may be along the anterior edge, posterior edge, right lateral and/or left lateral edges. The points of fusion may extend through the entire length of the two coaxial tubes or may be present at intervals. The inner coaxial tube may be located exactly in the center of the outer coaxial tube such that no additional device is required to center the lumen in the ETT or tracheobronchial tree. The MDA is a semi-flexible elongated conduit preferably without any concave or convex surface. The outer coaxial tube (8) has a lumen (7) with a distal orifice (9). The inner coaxial tube (10) terminates as a distal orifice (11). The right lateral and left lateral points of fusion between the outer tube (8) and the inner tube (10) are demonstrated (12). The ID (inner diameter), the OD (outer diameter), and the thickness of the walls of the two coaxial tubes may be variable, again depending on the adult of pediatric use. The ID of the inner coaxial tube may vary from 0.01 mm to 1.25 mm in size. The thickness of the wall of the inner tube the outer tube and the wall connecting with two tubes may vary from 0.01 mm to 1.25 mm. The ID of the outer coaxial tube, which may occupy up to 80% of the lumen of ETT, may be variable depending on the ETT through which it is introduced-adult or pediatric. The proximal end of the two coaxial tubes may be fused or are matable to a cylindrical metered dose inhaler (MDI) adapter. The MDI adapter has a peripheral part (13) that may perfectly fit into the adapter (6) on the horizontal limb of the VCA (4). The central hollow cylindrical part of the MDI adapter (14) is fused or is matable with the central or inner coaxial tube (10). The MDI adapter (14) has a proximal inlet for the nozzle (15) of the MDI canister (16). The MDI adapter (14) has gradually decreasing inner circumference so that the nozzle (15) of the MDI canister (16) locks into it after traversing some distance through the inlet port. Hence on actuation of MDI the medication and the propellant from the MDI canister is delivered at the distal tip of the inner coaxial tube (11) via the nozzle, MDI adapter and the inner coaxial tube. Another special feature of the MDI adapter is the ability of the device to be maneuvered into the right and left mainstem bronchi. This is made possible with the help of two elastic (stretchable) strings that run in the two lateral walls of the outer coaxial tubes at 3 o'clock and 9 o'clock positions (17, 19). The strings start at the distal tip of the outer coaxial tube and terminate at the proximal end into two rotator knobs (18,20) on the proximal surface of the peripheral part of the MDI adapter (14). Rotation of the right knob (18) turns the catheter towards the right mainstem bronchus and rotation of the left rotator knob (20) turns the catheter towards the left main bronchus. Hence, the aerosol medication particles can be delivered independently to each lung one at time. The MDA has numerous secondary orifices in the proximal ⅓ (21) and distal ⅓ (22) segments of the outer coaxial tube that are in communication with the lumen of the ETT, tracheobronchial tree, the VCA and hence the ventilator. This special feature of the device enables the delivery of medication to the tracheobronchial tree without any interference with the ventilatory function. The outer coaxial tube can occupy close to 90% of the ID of the ETT without any interference with the ventilatory function on account the secondary orifices.

FIG. 2 shows the longitudinal view of an alternative embodiment of 'AEROSOL DELIVERY APPARATUS III'. The major differentiating feature of this embodiment of the present invention is that the MDA has a single hollow cylindrical tubular structure. The inner coaxial tube is absent and instead there is a secondary cannulation in the wall of the MDA. The secondary cannulation terminates as a narrow orifice at the distal tip of the MDA and its proximal end is fused to MDI adapter.

FIG. 2 demonstrates the ETT (23) with a terminal lumen (24), the ETT adapter (25), the VCA (26) and the wye connector (27). The horizontal limb of the VCA (26) has an adapter/port (28) with a plug (29). The MDA (30), a hollow tubular structure, has a distal orifice (31). The tubular structure of MDA (30) terminates at its proximal end as an MDI adapter (34) with a central hollow structure (37). The MDI adapter (34) has two handles (35,36). Instead of an inner coaxial tube as demonstrated in FIG. 1, there is a secondary cannulation (32) that runs in the wall of the tubular structure of MDA (30). The secondary cannulation terminates as a narrow distal orifice (33) at the tip of the tubular structure (30). The proximal end of the secondary cannulation (32) is fused or is matable with the hollow portion of (37) of the cylindrical MDI adapter (34). The proximal end of the MDI adapter is designed to fit the nozzle (38) of MDI canister (39). The two handles (35,36) of the MDI adapter (34) are designed for the middle and index fingers to hold onto in order to facilitate the actuation of MDI canister with the thumb. On actuation of the MDI canister, the medication and the propellant that is generated at the tip of the nozzle is delivered to tip of the secondary cannulation (33) via MDI adapter (37) and secondary cannulation (32). The orientation (anterior, posterior, right or left lateral) of the secondary cannulation (32) and the distal orifice may be indicated by an arrow at the proximal end of the MDI adapter. As the patient on the ventilator is mostly in supine position, on introduction of MDA into the ETT through the port (28) of VCA (26), MDA would rest on the posterior surface of ETT or posterior surface of tracheobronchial tree when introduced into right or left mainstem bronchi. The distal orifice (33) would be close to the center of ETT if the ID of MDA is exactly half the ID of ETT and the orientation of the secondary cannulation is in the anterior direction. Hence, the OD of MDA could be adjusted depending on the size of the ETT through which it is introduced. The two elastic strings (40,42) at 3 o'clock and 9 o'clock positions of the tubular structure (30) terminate as two rotator knobs (41,43) on the proximal surface of the MDI adapter. The secondary orifices in the proximal ⅓ (44) and distal ⅓ (45) are demonstrated here.

Figure 2:
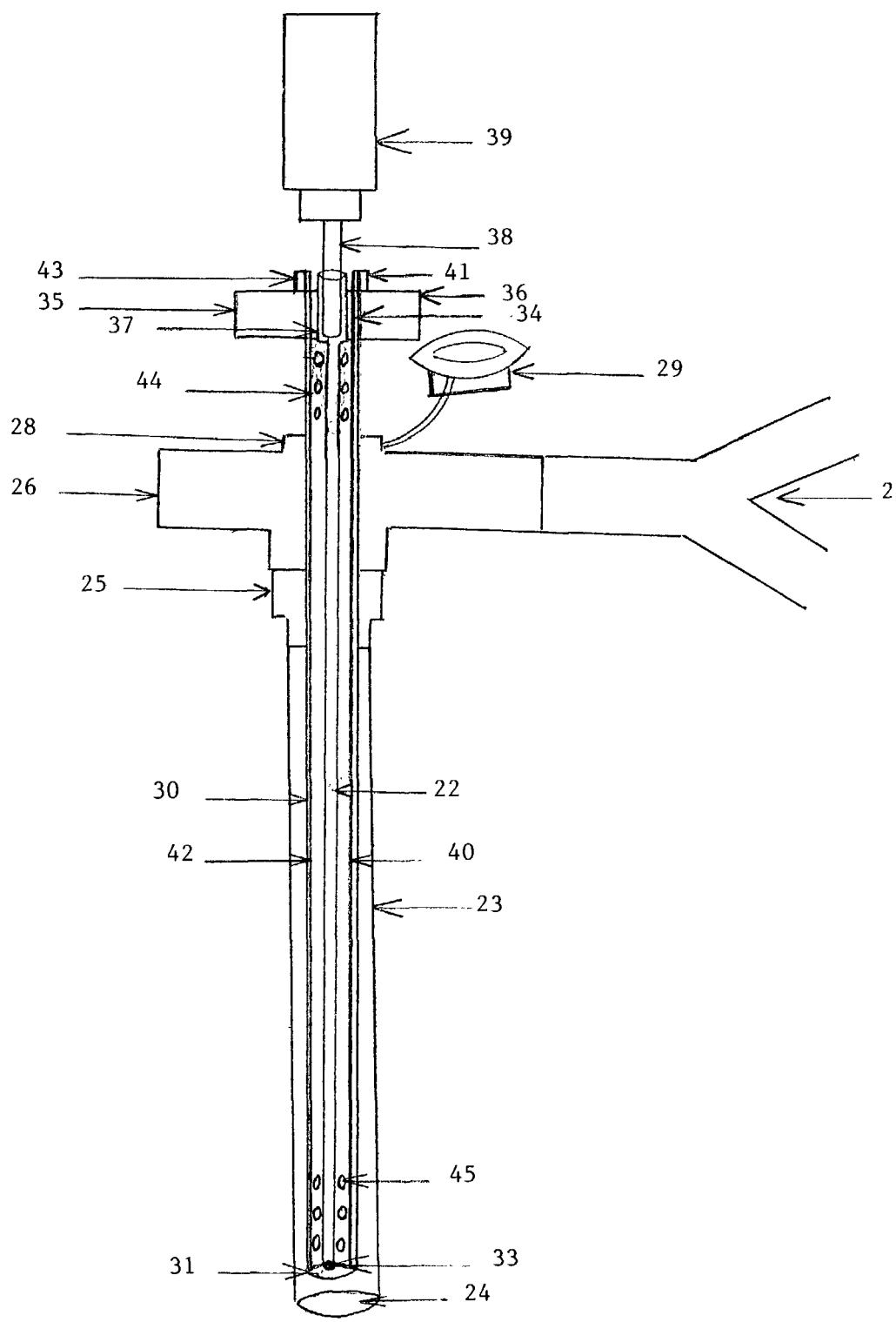
FIG. 2 is a plan view of the longitudinal length of Aerosol Delivery Apparatus III according to the first alternative embodiment of the present invention.
Figure 3:
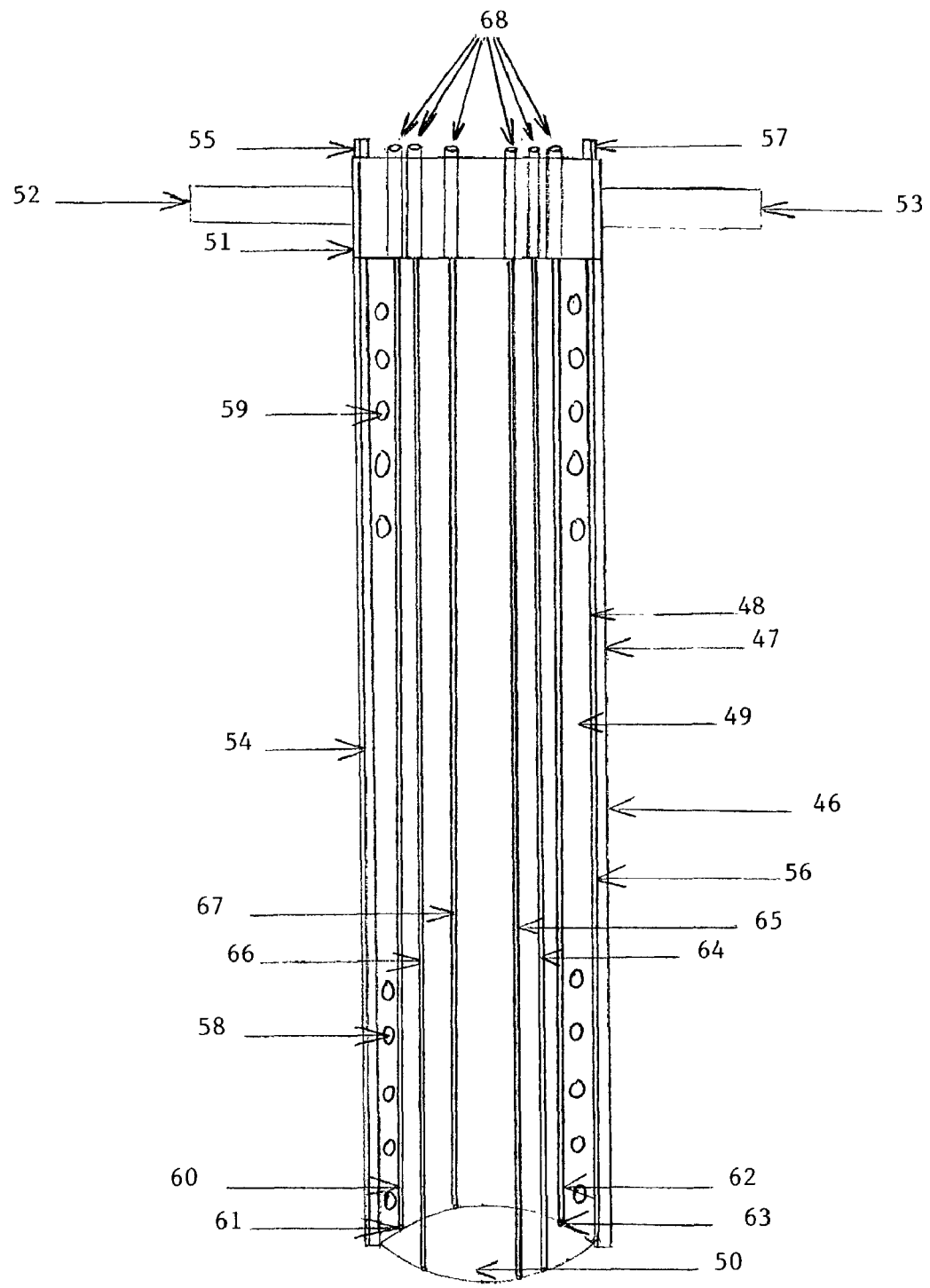
FIG. 3 is a plan view of the longitudinal length of Aerosol Delivery Apparatus III according to the second alternative embodiment of the present invention.

FIG. 3 is the longitudinal length of 'AEROSOL DELIVERY APPARATUS III' according to second alternative embodiment of the present invention. In FIG. 3, only MDA component of 'AEROSOL DELIVERY APPARATUS III' is demonstrated without VCA or ETT and its connections. Medication dispenser with adapter (MDA), a hollow cylindrical tubular structure (46) with a lumen (49) and a distal orifice (50) is demonstrated here. The tubular structure (46) fuses or is matable at its proximal end with a cylindrical adapter (51) that has a left handle (52) and a right handle (53) just as demonstrated in FIG. 2. The tubular structure (46) has an inner wall (48) and an outer wall (47). The two elastic strings, the left (54) and the right (56) that run their full course between the inner wall (48) and the outer wall (47) at 3 and 9 o'clock positions. The distal tip of each elastic string terminates at the tip of the tubular structure (46) and the proximal end terminates as a rotator knob, the left (55) and the right (57), on the proximal surface of the cylindrical adapter (51). As opposed to a single secondary cannulation as demonstrated in FIG. 2, there may be multiple secondary cannulations in the wall of the tubular structure (46). The number of secondary cannulations may vary from 2 to 6. The secondary cannulations may be located at 2 (62), 4 (64), 6 (65), 8 (66), 10 (60) and 12 o'clock (67) positions. Alternatively the cannulations may be located in different positions anywhere along the circular edge and not necessarily at regular intervals. Secondary cannulations terminate at the distal tip of MDA as narrow orifices, two of which are marked with arrows (61,63). The six secondary cannulations at their proximal end may fuse or are matable with six MDI adapters (68). The six MDI adapters (68) are located at 2, 4, 6, 8, 10 and 12 o'clock positions on the proximal surface of the adapter (51). The ID of the secondary cannulations as described in FIG. 2 may vary from 0.01 mm to 1.25 mm. Thickness of the wall of the tubular structure (46) may vary from 0.01 mm 1.25 mm. The OD of the MDA is preferably half the ID of ETT lumen, which would position the anterior secondary cannulation exactly in the center of ETT. Alternatively there may be two or three secondary cannulations as opposed six, which may split into three or two micrometric orifices respectively at the distal tip to give rise to six distal orifices. The presence of numerous secondary cannulations with distal orifices makes it possible to generate central as well as peripheral aerosol plumes, and hence avoiding tracheal and carinal impaction respectively. This may enable uniform distribution of aerosol particles in the distal tracheobronchial tree. There may be numerous secondary orifices in the proximal ⅓ (59) and distal ⅓ (58) segments of MDA. These orifices serve the same purposes as described in FIG. 1.

Figure 4:
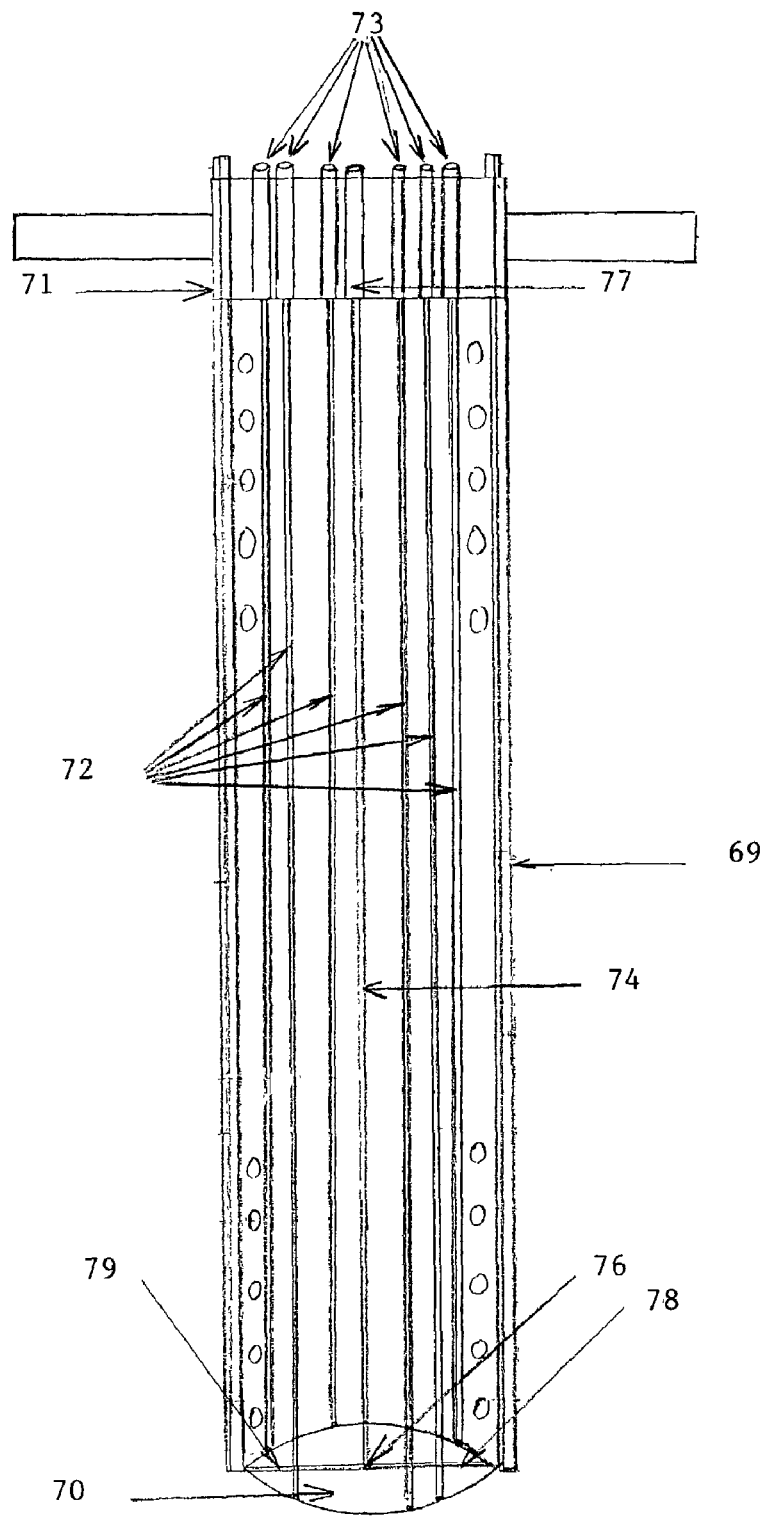
FIG. 4 is a plan view of the longitudinal length of Aerosol Delivery Apparatus III according to the third alternative embodiment of the present invention.

FIG. 4 is the longitudinal view of our 'AEROSOL DELIVERY APPARATUS III' according to third alternative embodiment of the present invention. FIG. 4 demonstrates the combined features of 'AEROSOL DELIVERY APPARATUS III' as described in FIGS. 1, 2 and 3. FIG. 4 demonstrates MDA without VCA or the ETT. FIG. 4 describes the longitudinal view of the MDA with two coaxial tubes: the outer (69) and the inner (74). The outer tube (69) has a distal orifice (70) and an inner coaxial tube has a distal orifice (76). Two tubes may be fused to each other at one or more points. Two points of fusion, the right lateral (78) and the left lateral (79) are demonstrated here. The purpose of fusion is to keep the inner coaxial tube in a fixed position in the center of the outer coaxial tube. There may be anterior and/or posterior points of fusion as well. There may be one (74) or more (72) secondary cannulations in the wall of MDA; if single, it should preferably be located in the anterior position and if more than one, the secondary cannulations may be located in 2, 4, 6, 8, 10 and 12 o'clock positions as described before. The outer tube (69) may be fused or matable with a cylindrical adapter (71). The central coaxial tube (74) and multiple secondary cannulations (72) may be fused or matable at the proximal end with MDI adapters (77 and 73 respectively). The MDI adapter (77) of the central coaxial tube may be located in the center of the adapter (71) and the multiple MDI adapters (73) of the multiple secondary cannulations (72) may be located at 2, 4, 6, 8, 10 and 12 o'clock positions on the proximal surface of the adapter (71). The left and the right handle of the MDI adapter (71), the elastic strings, the rotator knobs and the numerous secondary orifices as demonstrated just as in FIGS. 2 and 3.

Figure 5:
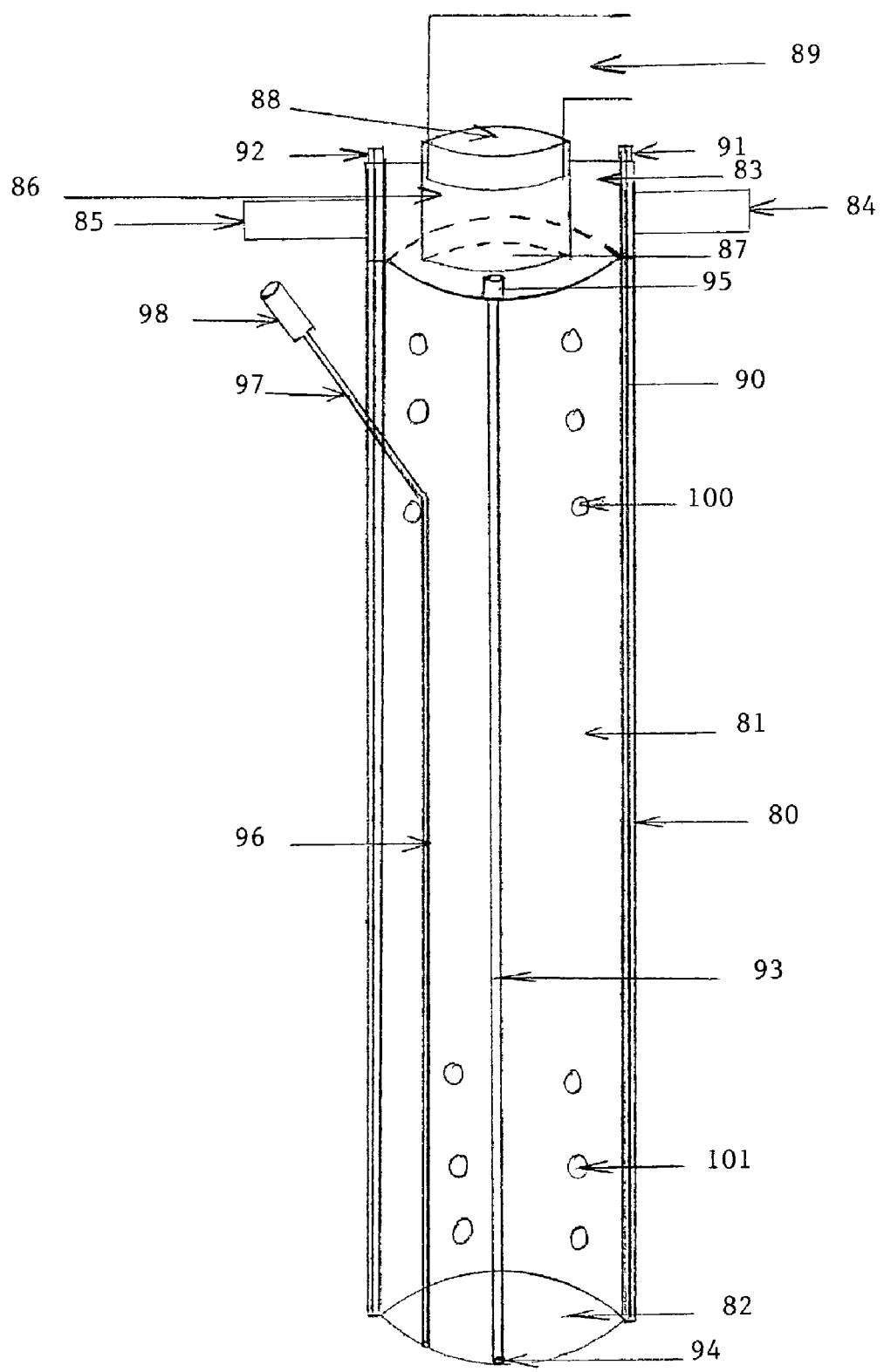
FIG. 5 is a plan view of the longitudinal length of Aerosol Delivery Apparatus III according to the fourth alternative embodiment of the present invention.

FIG. 5 is the longitudinal view of 'AEROSOL DELIVERY APPARATUS III' according to fourth alternative embodiment of the present invention. FIG. 5 demonstrates the longitudinal length of MDA just as described in FIG. 2 but with a modification, which enables the device to serve the dual functions of aerosol delivery as well as suction of respiratory secretions. The special feature of this device is that the proximal adapter (83) has a central hollow cylindrical part (86) with a proximal orifice (88) and a distal orifice (87). The distal orifice (87) communicates with the lumen of the cylindrical tubular structure (80) of MDA. The proximal orifice (88) may be connected to the suction source with the help of a connector (89). MDA (80) is a single hollow tubular structure with a distal orifice (82) and a central lumen (81). The tubular structure (80) of MDA is matable with the cylindrical adapter (83). In the wall of the tubular structure (80) there is a single secondary cannulation (93), which terminates at the distal tip of MDA as a narrow orifice (94). The proximal end of the secondary cannulation terminates as an MDI adapter (95). The MDI adapter (95) terminates on the peripheral rim of the cylindrical adapter (83). The right elastic string (90) and the two-rotator knobs (91,92) are also demonstrated. MDI adapter has two handles (84,85) for the middle and index fingers to hold onto in order to facilitate the actuation of MDI canister with the thumb. Numerous secondary orifices in the proximal ⅓ (100) and the distal ⅓ (101) of the tubular structure (80) are also demonstrated. An alternative course of the secondary cannulation (96) may also be possible. As opposed to running through the entire length of the tubular structure (80), the secondary cannulation may run a course in the wall of MDA for about ⅔ it's length. At this point it may exit the main tubular structure (80) of MDA as a semi-flexible narrow tubule (97), which may terminate at its proximal end as MDI adapter (98).

Figure 6:
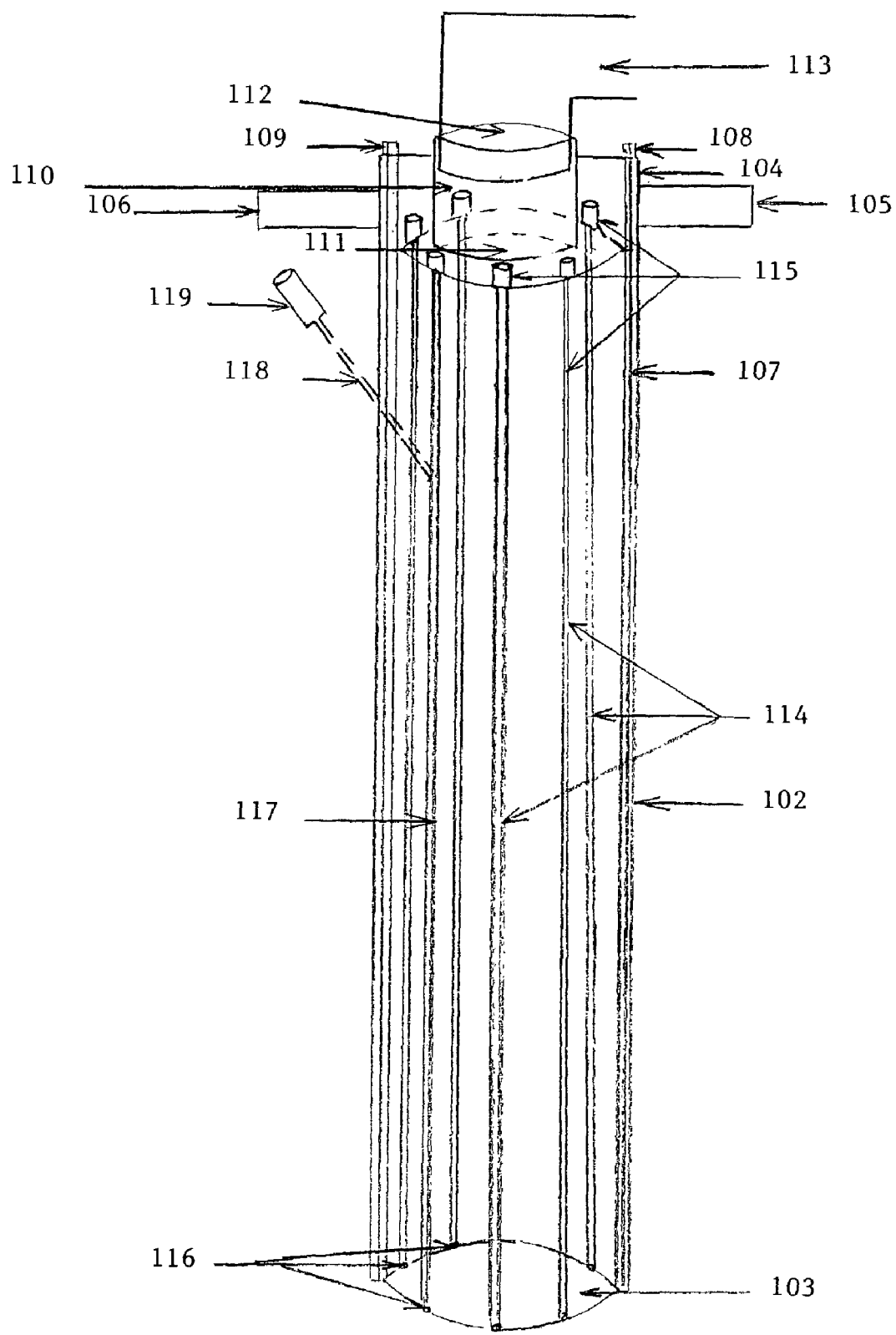
FIG. 6 is a plan view of the longitudinal length of Aerosol Delivery Apparatus III according to the fifth alternative embodiment of the present invention.

FIG. 6 is the longitudinal length of 'AEROSOL DELIVERY APPARATUS III' according to fifth alternative embodiment of the present invention. FIG. 6 combines the features of FIGS. 3 and 5. The MDA in FIG. 6 has a tubular structure (102) that terminates with a distal orifice (103). It fuses at the proximal end with an adapter (104), which has two handles, a right (105) and a left (106). The center of the adapter (104) is a hollow cylindrical structure (110) with a distal orifice (111) that communicates with the main lumen of the tubular structure (102) and a proximal orifice (112), which can be connected to the suction source through a connector (113). The elastic string (107) and the two rotator knobs are (108,109) are demonstrated here. There may be numerous (more than 1) secondary cannulations as described before in the wall of MDA (102). The numerous secondary cannulations (114) terminate at numerous distal narrow orifices (116). Secondary cannulations (114) terminate at proximal end as MDI adapters (115). MDI adapters may be located on the peripheral rim of the cylindrical adapter (104). There may or may not be secondary orifices in the proximal and distal ⅓ segments of the main tubular structure (103). An alternative course (117) of the secondary cannulation has also been demonstrated just as described in FIG. 5. The secondary cannulation may run a course in the main tubular structure (117) for about ⅔ the length of MDA (102) and then exit from the main tubular structure to emerge as a semi-flexible tubule (118) which may be fused or matable with MDI adapter (119). Hence, FIG. 6 demonstrates the ability of the device to serve the dual functions of a suction catheter as well as the delivery of aerosol particles of medication via central and peripheral plumes for uniform distribution in the tracheobronchial tree.

Figure 7A:
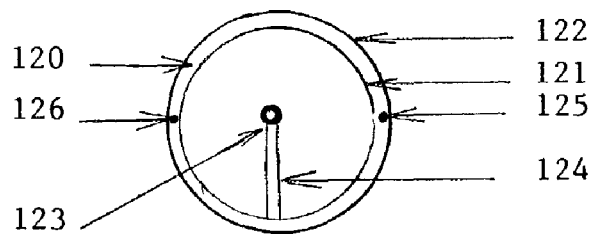
FIG. 7a is the expanded cross-sectional view of Aerosol Delivery Apparatus III according to the present invention as described in FIG. 1.

FIG. 7a is the expanded cross sectional view of 'AEROSOL DELIVERY APPARATUS III' according to the present invention as described in FIG. 1. The two coaxial tubes, the outer (120) and the inner (123) are demonstrated in FIG. 7a. The outer coaxial tube has an inner wall (121) and an outer wall (122). The inner coaxial tube (123) is fused to the inner wall (121) of the outer coaxial tube (120) in anterior location (124). The two elastic strings for directing the device into right and left mainstem bronchi are located at 3 o'clock, (126) and 9 o'clock (125) positions between the inner (121) and outer (122) walls of the outer coaxial tube (120).

Figure 7B:
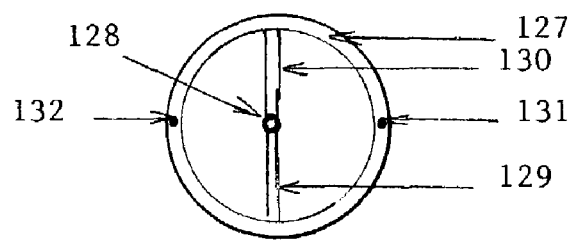
Figure 7C:
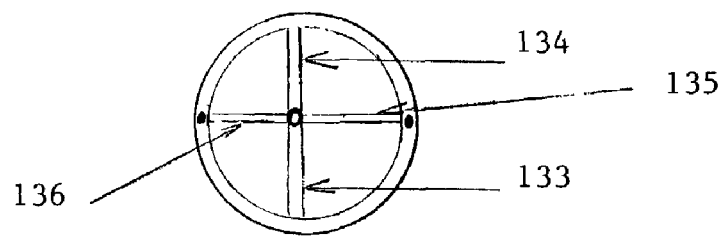

FIGS. 7b and 7c are the expanded cross sectional views of 'AEROSOL DELIVERY APPARATUS III' according to alternative embodiments of the present invention as described in FIG. 7a.

FIG. 7b demonstrates an outer coaxial tube (127), and an inner coaxial tube (128) and the two elastic strings (131,132). There are two points of fusion between the inner and the outer coaxial tubes—an anterior location (129) and a posterior (130).

FIG. 7c is the same as FIG. 7b but with four points of fusion between the inner and the outer coaxial tubes anterior (133), posterior (134) and two lateral (135,136).

Figure 8:
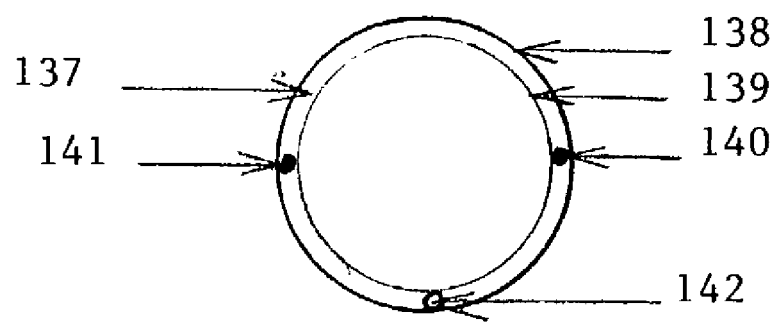
FIG. 8 is the expanded cross-sectional view of Aerosol Delivery Apparatus III according to the present invention as described in FIG. 2.

FIG. 8 is the expanded cross sectional view of 'AEROSOL DELIVERY APPARATUS III' according to the present invention as described in FIG. 2. The outer coaxial tube (137) has an inner wall (139) and an outer wall (138). The two elastic strings in 3 and 9 o'clock positions (141,140 respectively) and the secondary cannulation (142) in 12 o'clock position (142) between the inner (139) and the outer (138) walls of the outer coaxial tube (137) are demonstrated.

Figure 9:
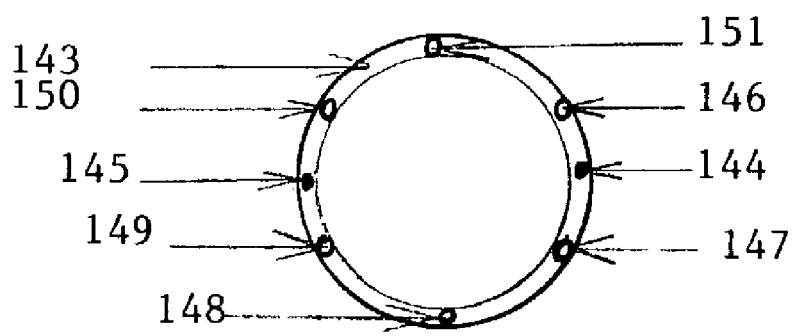
FIG. 9 is an expanded cross-sectional view of Aerosol Delivery Apparatus III according to the present invention as described in FIG. 3.

FIG. 9 is an expanded cross sectional view of the 'AEROSOL DELIVERY APPARATUS III' according to the present invention as described in FIG. 3. The outer coaxial tube (143), the two elastic strings at 3 o'clock (144) and 9 o'clock (145) positions, multiple secondary cannulations at 2 (146), 4 (147), 6 (148), 8 (149), 10 (150), 12 (151) o'clock positions between the inner and outer walls of the outer coaxial tube (143) are demonstrated. The number of secondary cannulations may vary from 2-6. Their positions may alternatively be located anywhere along the circular edge of the outer coaxial tube at regular or irregular intervals.

FIG. 10 is the expanded cross sectional view of 'AEROSOL DELIVERY APPARTUS III' according to the present invention as described in FIG. 4. The outer coaxial tube (152), and the two elastic strings in 3 o'clock (154) and 9 o'clock position (153) are demonstrated. There is an inner coaxial tube (161), which is fused to the inner wall of the outer coaxial tube (152) in anterior location (162). Multiple secondary cannulations in the wall of the outer coaxial tubes at 2, 4, 6, 8, 10 and 12 o'clock positions (155,156,157,158,159,160) are also demonstrated.

Figure 10A:
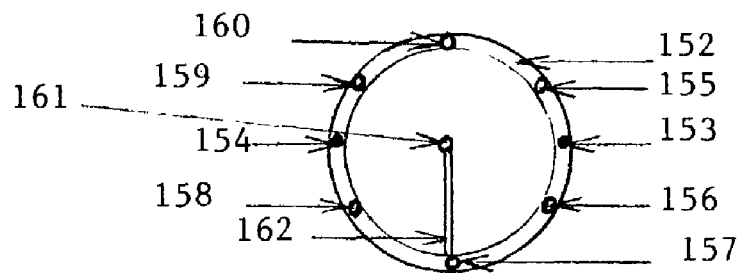
FIG. 10a is the expanded cross-sectional view of Aerosol Delivery Apparatus III according to the present invention as described in FIG. 4.
Figure 10B:
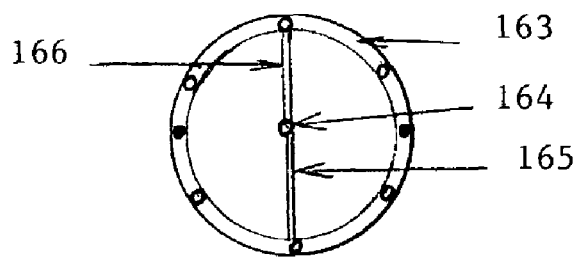
Figure 10C:
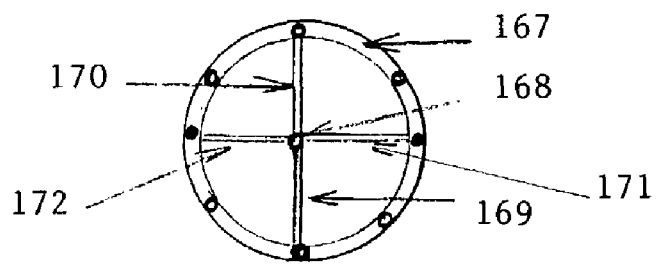

FIGS. 10b and 10c are the expanded cross sectional views of 'AEROSOL DELIVERY APPARATUS III' according to the alternative embodiments of the present invention as described in FIG. 10a. FIGS. 10b and 10c are identical to FIG. 10a except for the multiple points of fusion between the inner and the outer coaxial tubes. Inner coaxial tube (164) is fused to the outer coaxial tube (163) at two points of fusion in FIG. 10b anterior and posterior (165,166). In FIG. 10c the inner coaxial tube (168) is fused to the outer coaxial tube (167) at four points of fusion anteriorly (169) posteriorly (170) and the two lateral locations (171,172).

Figure 11A:
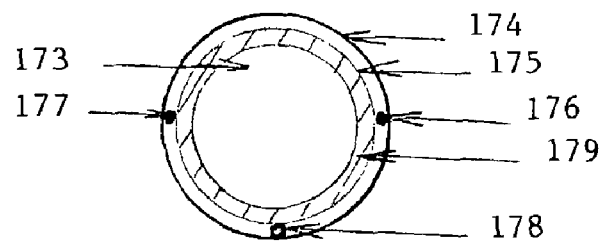
FIG. 11a is the expanded cross-sectional view of Aerosol Delivery Apparatus III (from the top) according to the present invention as described in FIG. 5.

FIG. 11a is the expanded cross sectional view (from the top) of the present invention as described in FIG. 5. The outer coaxial tube (174) fuses with the adapter (175) at the proximal end. The adapter has a solid peripheral part marked with stripes (179) and a central hollow part (173). The central hollow part (173) communicates with the lumen of the main tubular structure of MDA (174). The lumen (173) of the adapter can be connected to the suction source with the help of a connector. The two elastic strings (176,177) and the secondary cannulation (178) in anterior location in the wall of MDA are demonstrated. The secondary cannulation terminates as MDI adapter (not shown in this figure) on the proximal surface of the solid peripheral portion (179) of the adapter (175).

Figure 11B:
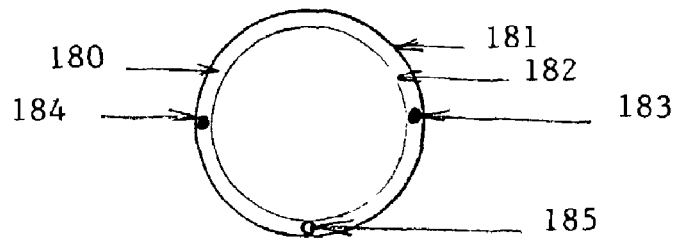
FIG. 11b is the expanded cross sectional view of Aerosol Delivery Apparatus III (from the bottom) according to the present invention as described in FIG. 5.

FIG. 11b is the expanded cross sectional view (from the bottom) of the present invention as described in FIG. 5. The main cylindrical tube of MDA (180) has an inner wall (182) and an outer wall (181) with two elastic strings at 3 o'clock and 9 o'clock positions (184,183) and the secondary cannulation (185) in anterior position between the inner (182) and the outer (181) walls of the outer coaxial tube (180) are demonstrated.

Figure 12A:
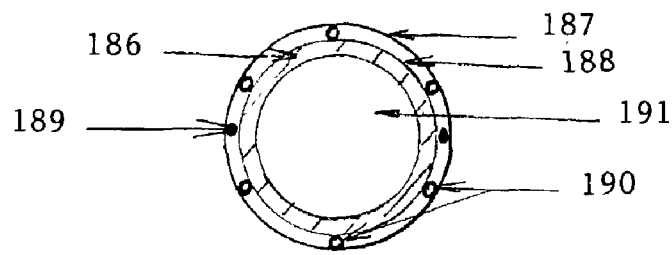
FIG. 12a and 12b are the expanded cross sectional view of Aerosol Delivery Apparatus III (from the top) according to the present invention as described in FIG. 6.

FIG. 12a is the expanded cross sectional view (from the top) of the present invention as described in FIG. 6. The main cylindrical structure of MDA (187) is fused with the adapter (188) at the proximal end. The peripheral solid part of the adapter (188) marked with stripes (186) and the lumen (191) are demonstrated. The two elastic strings, one of them marked with the arrow (189) and multiple secondary cannulations, two of them marked with an arrow (190) are also demonstrated in FIG. 12a.

Figure 12B:
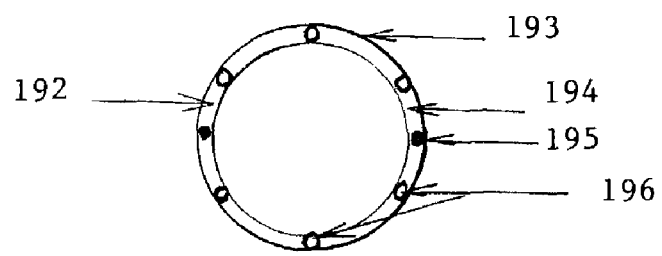

FIG. 12b is the expanded cross sectional view of the present invention as described in FIG. 6. The main cylindrical tube of MDA (192), the two elastic strings, one of them marked with an arrow (195) and multiple secondary cannulations, two of them marked with an arrow (196) between the inner wall (194) and the outer wall (193) of the main cylindrical tube (192) are demonstrated in FIG. 12b.

Figure 13A:
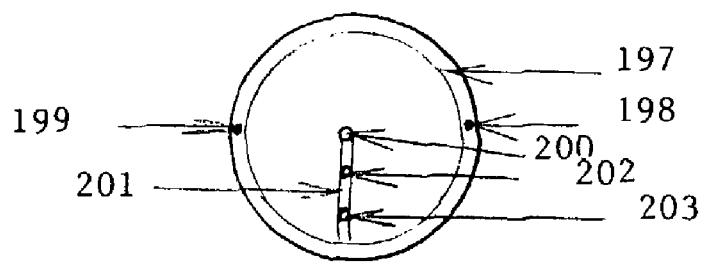
FIGS. 13a, 13b and 13c are the expanded cross sectional views of Aerosol Delivery Apparatus III according to the alternative embodiments of the present invention as described in FIGS. 7a, 7b and 7c respectively.
Figure 13B:
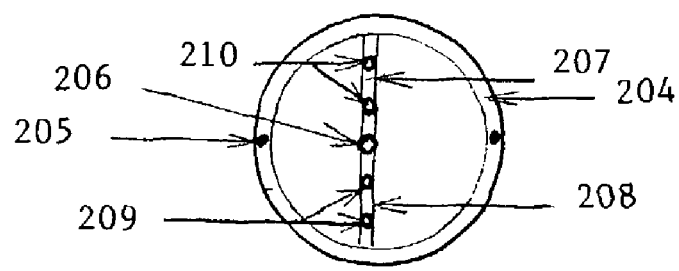
Figure 13C:
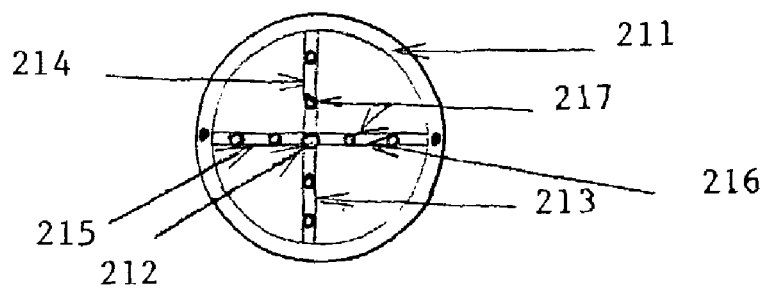

FIGS. 13a, 13b, and 13c are the expanded cross sectional views of the alternative embodiments of the present invention as described in FIGS. 7a, 7b and 7c respectively. The outer coaxial tube (197), the inner coaxial tube (200), the two elastic strings in 3 o'clock and 9 o'clock positions (199,198) and the anterior fusion (201) between the inner coaxial tube (200) and the outer coaxial tube (197) are demonstrated. The inner coaxial tube may split into two or more micrometric orifices at the distal tip (202,203), which may be located in the wall of fusion between the inner and outer coaxial tubes.

FIG. 13b demonstrates the outer coaxial tube (204), two elastic strings one of them marked with an arrow (205), the inner coaxial tube (206), the anterior wall of fusion (208) and the posterior wall of fusion (207) between the inner and the outer coaxial tubes. The inner coaxial tube may split into multiple micrometric openings that may be located in the anterior wall (209) and the posterior wall (210) of fusion between the inner and the outer coaxial tubes.

FIG. 13c demonstrates the outer coaxial tube (211), the inner coaxial tube (212), the anterior (213), the posterior (214), and the two lateral walls (215,216) of fusion between the inner and the outer coaxial tubes. The inner coaxial tube (212) may split into the multiple micrometric openings (217) along the anterior, posterior and the two lateral walls. The central coaxial tube may split into two or more than two openings along each wall of fusion.

Figure 14A:
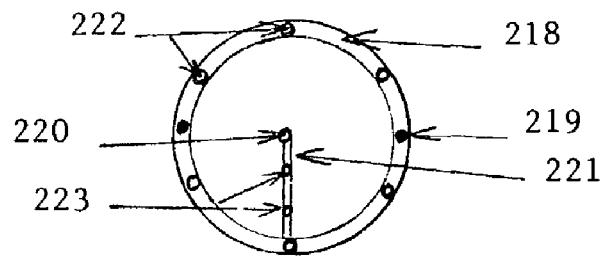
FIGS. 14a, 14b and 14c are the expanded cross sectional views of Aerosol Delivery Apparatus III according to the alternative embodiments of the present invention as described in FIGS. 10a, 10b and 10c.
Figure 14B:
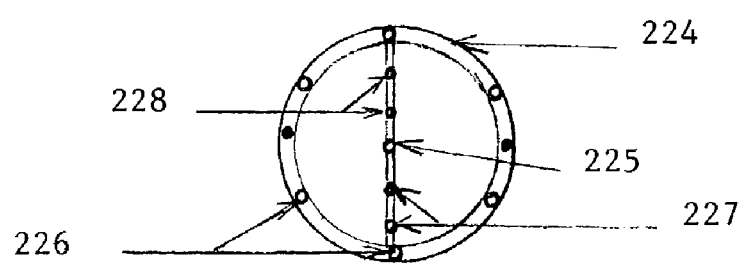
Figure 14C:
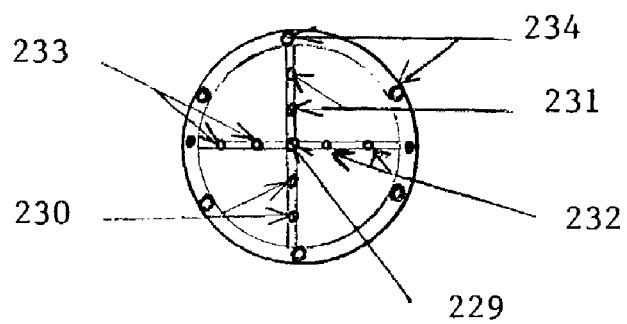

FIGS. 14a, 14b and 14c are the expanded cross sectional views of the alternative embodiments of the present invention as described in FIGS. 10a, 10b and 10c respectively. The outer coaxial tube (218), the elastic strings in 3 o'clock and 9 o'clock positions (219), the inner coaxial tube (220), the anterior wall of fusion between the inner and the outer coaxial tube (221), the multiple secondary cannulations (222) in the wall of outer coaxial tube (218) and multiple micrometric openings in the anterior wall of fusion (223) that may arise from the inner coaxial tube (220) are demonstrated in FIG. 14a.

FIG. 14b demonstrates the outer coaxial tube (224), the inner coaxial tube (225), multiple secondary cannulations (226) in the wall of the outer coaxial tube (224) and multiple micrometric openings (227,228) along the anterior and posterior walls of fusion between the inner and the outer coaxial tubes.

FIG. 14c demonstrates the inner and the outer coaxial tubes with the elastic strings at 3 o'clock and 9 o'clock positions and multiple secondary cannulations (234) in the wall of the outer coaxial tubes. The inner coaxial tube (229) may split into two or more micrometric openings along the anterior wall of fusion (230), the posterior wall (231), and the two and the lateral walls in 3 o'clock position (233) and 9 o'clock position (232).

Figure 15A:
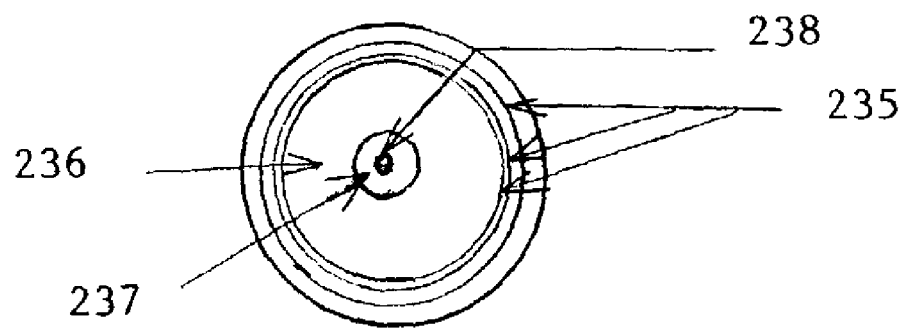
FIG. 15a is the expanded cross sectional view of the MDI adapter (from the top) as described in FIGS. 1-6 of the present invention.

FIG. 15a is the expanded cross sectional view of the MDI adapter (from the top) as described in FIGS. 1-6. FIG. 15a demonstrates the inlet of MDI adapter with multiple concentric rings (235) with decreasing circumference such that the nozzle of the MDI canister locks into the innermost concentric ring (236). The terminal orifice (237) of MDI adapter fuses or is matable with the proximal end of the inner coaxial tube (238) as demonstrated in FIG. 1 or the proximal end of the secondary cannulation (238) as demonstrated in FIG. 2.

Figure 15B:
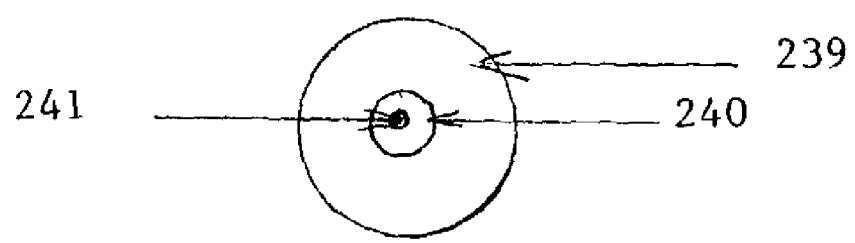
FIG. 15b is the expanded cross sectional view of the MDI adapter (from the bottom) as described in FIGS. 1-6 of the present invention.

FIG. 15b is the expanded cross sectional view of the MDI adapter (from the bottom) as described in FIGS. 1-6 of the present invention. Nozzle of the MDI canister locks into the innermost ring (239). The distal orifice of the MDI adapter (240) fuses or is matable with the proximal end of the inner coaxial tube (241) as demonstrated in FIG. 1 or the proximal end of the secondary cannulation (241) as demonstrated in FIG. 2.

Figure 16:
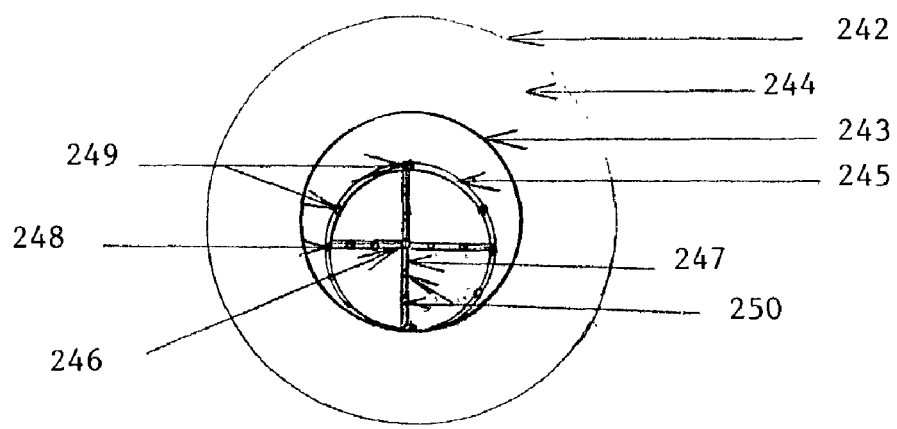
FIG. 16 is the expanded cross sectional view of the trachea, endotracheal tube and Aerosol Delivery Apparatus III incorporating all the features of the present invention as described in FIGS. 1-15.
Figure 17A:
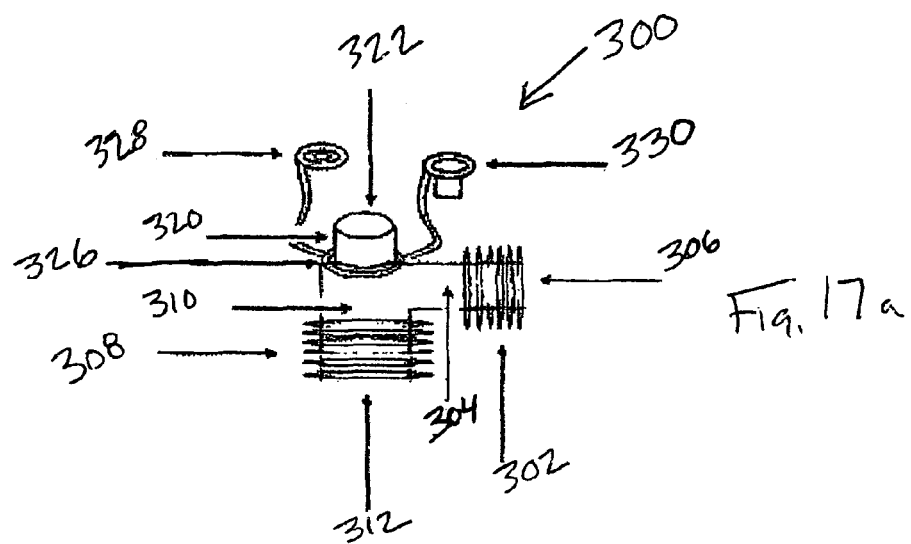
FIG. 17a is a side perspective view of a ventilator connector with adapter (VCA) according to one embodiment of the present invention.
Figure 17B:
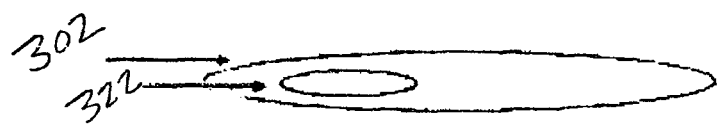
Figure 17C:
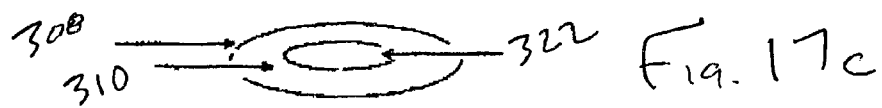

FIG. 16 is the expanded cross sectional view of the trachea, ETT and 'AEROSOL DELIVERY APPARATUS III' incorporating all the features described above in FIGS. 1-15. The inner wall of the trachea (242), the lumen of the trachea (244), the inner wall of the ETT (243) after the balloon of the ETT is inflated is demonstrated in FIG. 16. MDA portion of AEROSOL DELIVERY APPARATUS III (245) is demonstrated in the wall of the ETT (243). The outer coaxial tube (245), the inner coaxial tube in the center (246), and the four points of fusion the anterior (247), posterior (249) and the two lateral (245) between the inner (246) and outer coaxial tubes (245), the secondary cannulations (249) in the wall of the outer coaxial tube (245), the elastic strings at 3 o'clock (248) and 9 o'clock positions, and the multiple micrometric openings (250) of the inner coaxial tube (246) along the anterior, posterior, and/or two lateral walls of fusion between the inner and the outer coaxial tubes are all demonstrated in FIG. 16. The device may incorporate one, more than one or all the features as shown in FIG. 16. In addition, the device may also include a special syringe, the terminal injection port of which may have a configuration identical to the nozzle of MDI. This will enable the MDI port to be used for delivery of any liquid medication to the respiratory system via a manually operated syringe.

FIGS. 17*a*-*c* illustrate a ventilator connector with adapter (VCA) 300 according to one exemplary embodiment of the present invention. The VCA 300 is generally L-shaped. The VCA 300 has a horizontal limb 302 with a lumen 304 and a terminal end 306 for connection to a corrugated tube for the ventilator (not shown). The VCA 300 has a vertical limb 308 with a lumen 310 and a terminal end 312 for connection to an endotracheal tube (ET tube) 314 (FIG. 19). There is an adapter 320 on the horizontal limb 302 of the VCA 300 and the adapter 320 includes a lumen 322. The inner circumference of the cylindrical adapter 320 is designed such that the outer circumference of a distal cylindrical medicament dispenser adapter (MDA) 400 (described with reference to FIG. 18*a*-*c*) tightly fits into it. There is a plastic or rubber ring 326 around the adapter 320 with a cap 328 or a plug 330 that locks into the adapter 320 to make an air tight seal when MDA 400 is not in connection with VCA 300. The purpose of the VCA 300 is to ensure that the lumen 322 of the adapter 320 is axially aligned with the lumen 310 of the vertical limb 308. This will ensure that a semi-rigid cannula 410 of the MDA 400 can be easily manipulated through the lumen of the ET tube 314 to terminate distally beyond the tip of the ET tube 314.

FIG. 17*b* represents a cross-sectional view of the horizontal limb 302 of the VCA 300 (top and bottom views), demonstrates the horizontal limb 302 and the adapter lumen 322. FIG. 17*c* represents a cross-sectional view of the vertical limb 308 of the VCA 300 (top and bottom views), demonstrates the vertical limb 308, its lumen 310 and the adapter lumen 322. FIG. 18*a*-*c* illustrate the MDA 400. FIG. 18*a* is an oblique view of the MDA 400, is generally in the shape of a cylinder that is defined by a proximal cylinder portion 420 with a greater circumference than a distal cylinder 430 portion. The inner circumference of distal cylinder portion 430 is designed to fit outer circumference of a cylindrical nozzle 510 of an MDI 500 (described with reference to FIG. 19). The outer circumference of distal cylinder portion 430 is designed to fit the inner circumference of VCA adapter 320. The distal cylinder portion 430 continues distally for 1-2 mm and tapers to a tip 432 to reach an ID of a pinhole opening 434 which marks the origin of a semi-rigid cannula 410. The semi-rigid cannula 410 continues distally for a variable length to terminate as a pinhole opening 411. The ID of the cannula and pinhole tip could vary from 0.15 mm to 2.0 mm. The length of the cannula 410 could vary depending on the size of the ET tube 314 such that it terminates approximately ½ cm distal to the tip of the ET tube 314 (approximately 38 cm for a full adult size ET tube 314). The rigidity of the cannula could be modified by changing the thickness of the wall and using a variety of plastic materials in order to allow manipulation within the lumen of the ET tube 314 avoiding the fling phenomenon. Wrapped around the center of MDA 400 is a plate like annular flange or support 440. This is an optional feature of the present invention. This annular support 440 rests on top of the VCA adapter 320 when the distal cylinder portion 430 of the MDA 400 fits into it. The annular support 440 is an additional safety measure to ensure that MDA 400 does not slip into the inspiratory circuit.

Figures 18A, 18B:
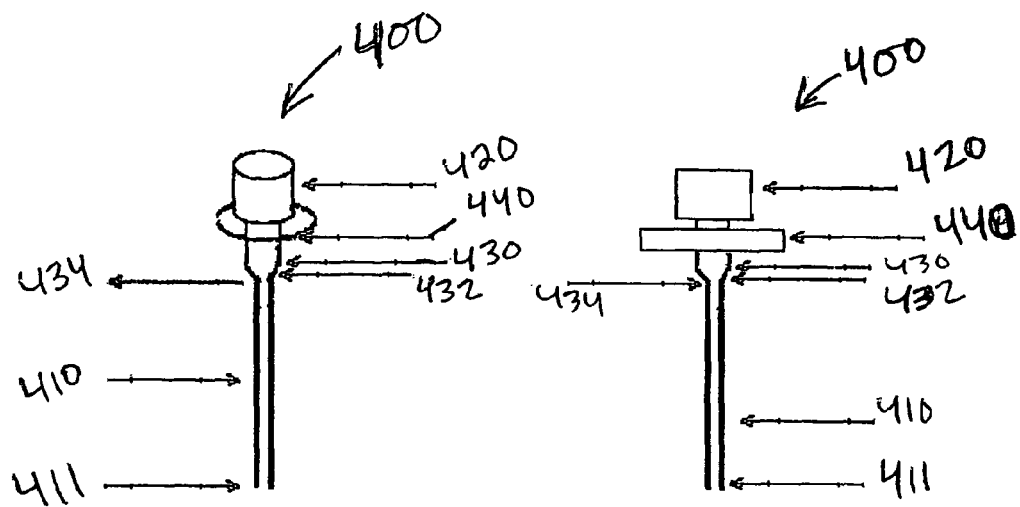
Figure 18C:
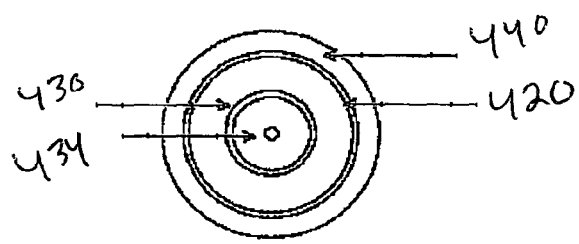

FIG. 18b represents a side elevation view of the MDA 400. FIG. 18c is a cross-sectional view of the MDA 400 and depicts the relationship between the proximal cylinder portion 420, the distal cylinder 430 portion, the pinhole opening 434 and the optional annular support 440 are shown.

Figure 19:
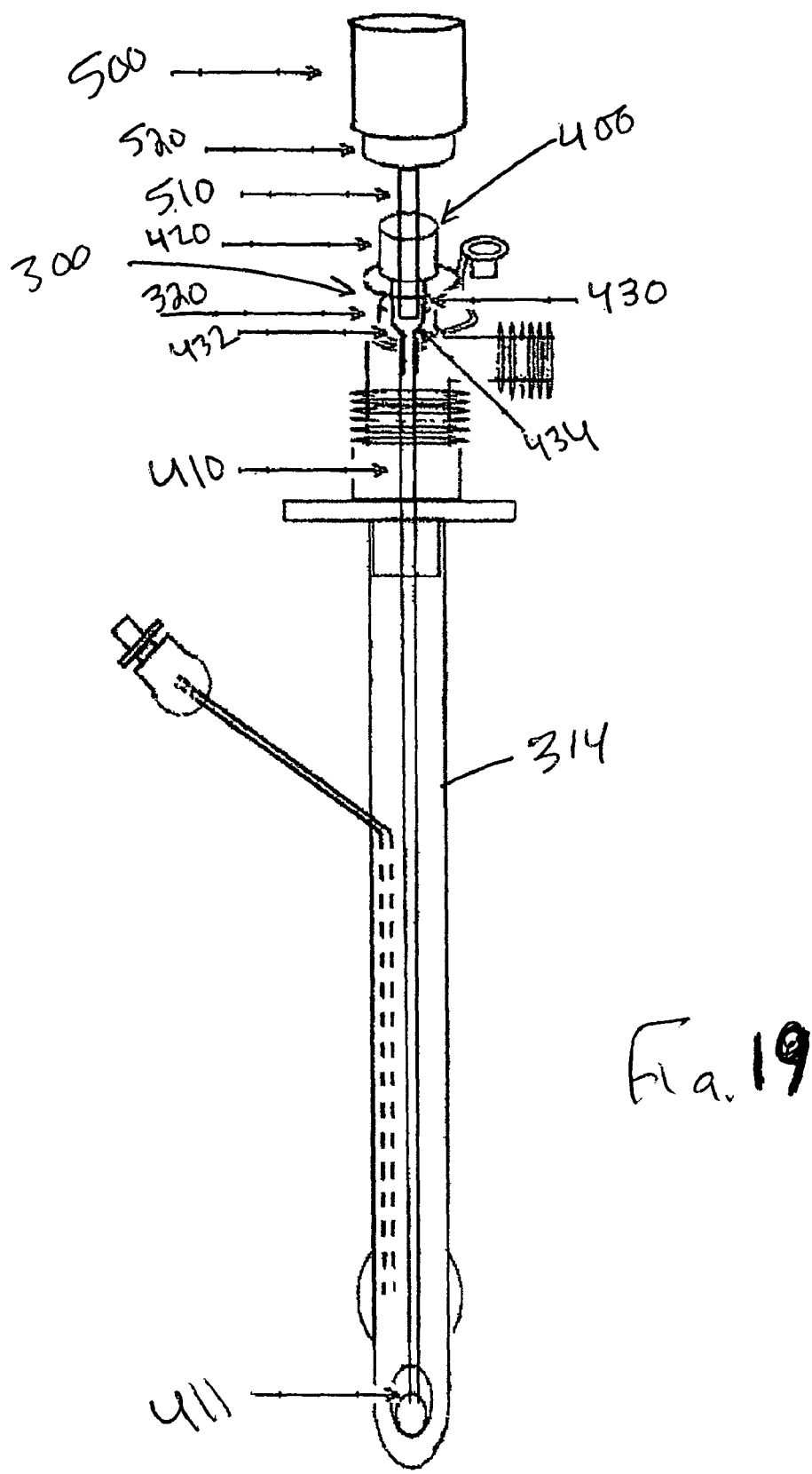
FIG. 19 is a side perspective view of the VCA and MDA combined with an endotracheal tube.

FIG. 19 is a side perspective view of a combination of the MDA 400 and VCA 300 with the endotracheal tube 314. The VCA 300 and the MDA 400 stay disconnected at all times unless the delivery of medication is required. The VCA adapter 320 remains plugged (sealed airtight) at all times. When ready to deliver the medication, the VCA adapter 320 is unplugged and the semi rigid cannula 410 is manipulated distally all the way through the lumen of the ET tube 314 to reach its tip. Finally at this point, a connection is made between the distal cylinder portion 430 of the MDA 400 and VCA adapter 320. The nozzle 510 of an MDI cannister 520 of the MDI 500 can now be plugged into the distal cylinder portion 430 (MDA adapter). An MDI valve is actuated by pressing the MDI 500 with a thumb or the like and aerosol particles are generated and delivered to the terminal end of the cannula 410. MDA 400 and VCA 300 should be disconnected immediately after delivery of medication and VCA adapter 320 re-plugged. In case the VCA 300 and MDA 400 are not disconnected, there may be an increase in the airway pressure (increased resistance) in the circuit due to reduced radius of the lumen.

Particle Size, Plume Characteristics and Drug Delivery

Effective drug delivery is closely related to particle size. Larger particles may provide a greater total drug delivery; however, a uniform distribution of medication in the distal tracheobronchial tree requires particle size distribution in the respirable range (<5 microns). Besides particle size, the drug delivery rate and distribution is also a function of the site of generation of the aerosol particles and the characteristics of the aerosol plume. Even though the size of aerosol particles generated in case of a suspension of pulverized powder medication in a liquid propellant is predetermined and is a function of the size of the crushed solid particles of powder medication, the drug delivery rate and distribution through Aerosol Delivery Apparatus III will be tremendously influenced by the features of the inner coaxial tube and secondary cannulation(s) and the terminal orifice(s) at their tips. The critical features of secondary cannulations are its length, ID, shape and orientation (central vs. peripheral and anterior vs. posterior, right lateral, left lateral and/or combination of the same), trajectory of the cannulations and (of the device and the material used to manufacture the device i.e. polymer, silicone, teflon etc). The features of the distal orifice that may play a role in distribution of aerosol particles are it's location, orientation, shape, and ID. All the aforementioned features will influence the total dose distribution, particle size and plume characteristics (geometry, velocity and orientation) and hence the distribution of the particles in the tracheobronchial tree. For the purpose of this discussion, the inner coaxial tube and secondary cannulation in the wall of the outer coaxial tube of 'Aerosol Delivery Apparatus III' will be referred to secondary cannulations.

There are numerous varieties of plastic materials that are used to manufacture 'Aerosol Delivery Apparatus III'. Some examples of the same are thermoplastics (polyvinyl chloride, polyethylene, polypropylene), silicone, teflon, tefzel etc. Even in the categories mentioned there are over 250 subcategories of manufacturing materials. Since the differences in the compliance and coefficient of friction materials could influence the delivery of aerosol medication, the secondary cannulation(s) may be co extruded using a compound or a polymer different from the one used to manufacture the outer coaxial tube of MDA. The co extrusion may optimize the physical properties of the secondary lumen(s) and maximize aerosol delivery. Examples of some co extrusions may be—PVC and teflon, PVC and polypropylene, PVC and silicone, PVC and polyethylene, etc. Aerosol Delivery Apparatus III may be disposable or reusable depending on the material used in its manufacture. The ventilator connector with adapter (VCA) may form a permanent part of the connection and medication dispenser with adapter (MDA) may be retained in a sterile sheath connected to the proximal end of the VCA so that it could be reinserted.

In our invention, the ID of the secondary cannulation(s) may be uniform throughout or may be tapered along the entire length. Alternatively, it may be uniform in the proximal part and tapered near the distal part. The ID of the secondary lumen may vary from 0.01 mm to 1.25 mm. A narrow ID of the secondary cannulation is very important for the aerosol medication to reach the distal tip of the secondary cannulation over approximate length of 30 cm or more of Aerosol Delivery Apparatus III. If the ID of secondary cannulations is too narrow throughout the length, it may pose a significant resistance to the flow of medication and impede aerosol delivery. If ID is too big, a significant portion of the medication may be deposited in MDA and hence affect the total dose delivery. Hence, designing a specific ID for each length of MDA device may be critical in total drug delivery.

Another very important feature is the course (trajectory) of the secondary cannulations. The trajectory may be directed from the outer wall to the inner wall; alternatively the secondary cannulation may stay closer to the outer wall throughout; closer to the inner wall throughout; or it may stay closer to the outer wall for the most part and may be redirected towards the inner wall near the distal part of the outer coaxial tube. A change in the plane of the secondary cannulation in the distal part of the outer coaxial tube (range 1 mm-20 mm) will change the orientation of the secondary lumen by approximately 5 to 45 degrees. The preferable change in the angle, however, may be 10-20 degrees only in order to prevent tracheal and/or carinal impaction losses. In another modification of our invention, the secondary cannulation may run inside the primary lumen on the inner wall or it may run on the surface of the outer wall of the outer coaxial tube. Secondary cannulations may all be identical or different from each other with respect to the features described.

The distal orifice(s) in our invention may also have numerous variations. The distal orifice of the secondary cannulation is located at the tip of the outer coaxial tube, preferably not in communication with its primary lumen and not protruding beyond its distal tip. The shape of the distal orifice is preferably circular; however, the shape may be semi circular, lunar, etc. The ID of the distal orifice, which may vary from 0.01 mm to 1.25 mm, may be the same or different from the ID of the secondary cannulation. The ID of the distal orifice may be made smaller or larger than the ID of the secondary cannulation; alternatively there may be a flare at the distal tip of the secondary cannulation in order to alter the geometry and velocity of the plume. The location of the orifice may be closer to the inner wall or outer wall or it may be in the center of the wall of the outer coaxial tube. The distal orifices may all be identical or different from each other with the respect to the features described.

The characteristics of aerosol plume may be one of the most important features that may influence uniform distribution of aerosol particles in the tracheobronchial tree. An aerosol plume (if generated proximal to the ETT or in the lumen of the ETT) will result in impaction losses on the ETT. An aerosol plume, if generated beyond the ETT as would be the case in our device may result in impaction losses on the tracheal wall or carina depending on the characteristics of the plume central vs. eccentric, narrow vs. wide, slow or softer vs. fast. In our invention various permutations and combinations of different characteristics of secondary cannulations and their distal orifices result in generation of multiple aerosol plumes that combine the different characteristics of the plume i.e. geometry, velocity, and orientation that enables uniform distribution of aerosol particles in the tracheobronchial tree. Of note is that the circular edge of ETT after inflation of the distal balloon in the lumen of trachea is a few millimeters away from the tracheal wall and so would be the secondary cannulations located in the wall of MDA.

The lateral location of some orifices would direct the plume either to the right or the left lung. This actually may be of tremendous benefit if one wants preferential delivery of medication to one lung, which has the pathology.

It is noted that the illustration (drawings) and description of the preferred embodiments have been provided merely for the purpose of explanation and although the invention has been described herein with reference to particular means, materials and embodiments, the invention is not intended to be limited to the particulars disclosed herein; rather the invention intends to all functionally equivalent structures, methods and uses such as are within the scope of the appended claims.

What is claimed is:

1. An aerosol delivery device comprising:
   a ventilator connector that is configured to mate with a conduit that leads to a ventilator for permitting inhalation and exhalation by a patient, the ventilator connector having a hollow first leg and a hollow second leg that is formed at an angle relative to the first leg, the first leg including an adapter that is defined by a hollow body that defines a lumen that is axially aligned with a lumen defined by the second leg;
   a medicament dispenser containing medication in aerosol form that is selectively delivered through a distal orifice of a nozzle of the dispenser;
   a medicament dispenser connector that is configured to be sealingly mated to the medicament dispenser and in communication with an endrotracheal tube, the medicament dispenser connector including a proximal hollow body portion that is configured to sealingly mate with a dispenser element of the medicament dispenser so as to fluidly link the two together;
   an elongated cannula portion extending from the proximal hollow body portion of the medicament dispenser connector, the cannula portion comprising a tubular structure that is defined by a main lumen and inner and outer walls; and
   a plurality of secondary orifices that are formed in proximal and distal segments of the tubular structure of the cannula portion, said secondary orifices being open along both the inner wall and the outer wall of the tubular structure and being in direct fluid communication with the main lumen,
   wherein the cannula portion has a plurality of secondary medication delivery conduits each of which has a lumen and an orifice that are fluidly connected to the medicament dispenser connector, said secondary medication delivery conduits being formed in the cannula portion between the inner and outer walls of the cannula portion and extending at least along a length thereof such that each lumen of the secondary medication delivery conduit is fluidly separated from the main lumen of the cannula portion,
   wherein in a dispensing mode, aerosol particles generated by the medicament dispenser are separately delivered through the main lumen of the cannula portion, as well as through the lumens of the secondary medication delivery conduits and through the secondary orifices into the endotracheal tube and into lungs of the patient such that a central aerosol plume is generated from the main lumen of the cannula portion and peripheral aerosol plumes are generated from the lumens of the secondary medication delivery conduits.

2. The aerosol delivery device of claim 1, wherein the ventilator connector is in the shape of an L-shaped connector and the first leg is a horizontal leg and the second leg is a vertical leg.

3. The aerosol delivery device of claim 1, wherein the angle between the first and second legs is substantially 90 degrees.

4. The aerosol delivery device of claim 1, further including a connector ring disposed about the hollow body and including a sealing member attached thereto at an end of an elongated connecting member that extends between the connector ring and the sealing member.

5. The aerosol delivery device of claim 4, wherein the sealing member comprises one of a removeable cap and a removeable plug.

6. The aerosol delivery device of claim 1, wherein a proximal end of the cannula portion is fluidly connected to an intermediate hollow body portion that has a tapered construction and is configured to be received in the adapter of the ventilator connector such that a tight frictional fit results therebetween, the intermediate body portion being fluidly connected at an opposite end to a proximal hollow body portion.

7. The aerosol delivery device of claim 6, wherein the medicament dispenser connector includes a locating member that sits against the adapter of the ventilator connector when the medicament dispenser connector and the ventilator connector are mated together so as to restrict the degree of insertion of the cannula in the adapter and the second leg.

8. The aerosol delivery device of claim 7, wherein the locating member comprises an annular flange that is disposed radially about the intermediate body portion.

9. The aerosol delivery device of claim 1, wherein an inner diameter of the cannula portion is selected such that particles generated by the medicament dispenser and delivered to the proximal end of the cannula portion are delivered to a distal end of the cannula portion in aerosolized form.

10. The aerosol delivery device of claim 1, wherein the axes of secondary orifices intersect with the axis of secondary medication delivery conduits.

11. The aerosol delivery device of claim 1, wherein the main lumen of the cannula portion and the lumens of the secondary medication delivery conduits are longitudinally oriented and parallel along at least a length of the tubular structure of the cannula portion.

12. The aerosol delivery device of claim 1, wherein the number of the secondary medication delivery conduits is in a range of 2 to 6.

13. A medication delivery system comprising:
   an MDI device for delivering aerosolized medication, the MDI device having a nozzle;
   an MDI adapter that is constructed to receive and mate with the nozzle of the MDI device, the MDI adapter including;
      a first elongated hollow tube that includes a main lumen that extends along a longitudinal length thereof, the hollow tube being defined by inner and outer walls; and
      a plurality of secondary medication delivery conduits each of which has a lumen that extends a length of the hollow tube and is formed internally within the tubular wall between the inner and outer walls, the lumen of the second medication delivery conduits being fluidly separated from the main lumen, wherein at least some of the secondary medication delivery conduits include proximal orifices at a proximal end of the hollow tube that are fluidly connected to the MDI device;
   wherein at least one secondary medication delivery conduit has an upper portion that is angled and extends through the elongated hollow tube and terminates at its proximal end in an adapter that is freely accessible along an exterior of the hollow tube, the angled portion being formed of a semi-flexible material;
   wherein the MDI adapter is configured to be fluidly mated with a ventilator adapter that is configured to connect to the ventilator device and be positioned so that it is axially aligned and in fluid communication with the proximal orifices of the secondary medication delivery conduits, the MDI adapter having an inlet port that is adapted to mate with the MDI device and is configured to be received within a central bore of an endotracheal tube and isolation of the secondary medication delivery conduits permits aerosolized medication to be delivered to the patient without interference from the delivery of air through the endotracheal bore.

14. A medication delivery system according to claim 13, comprising a mechanism for controllably steering the elongated hollow tube of the MDI adapter, wherein steering of the elongated hollow tube causes bending on the elongated hollow tube in at least two directions.

* * * * *